United States Patent
Hueter et al.

(10) Patent No.: US 11,882,828 B2
(45) Date of Patent: Jan. 30, 2024

(54) MOSQUITO VECTOR CONTROL COMPOSITIONS, METHODS AND PRODUCTS UTILIZING SAME

(71) Applicant: Syngenta Participations AG, Basel (CH)

(72) Inventors: Ottmar Franz Hueter, Stein (CH); Natalie Anne Miller, Stein (CH); Philip Wege, Bracknell (GB); Mark Hoppe, Stein (CH); Peter Maienfisch, Stein (CH); Michael Drysdale Turnbull, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 766 days.

(21) Appl. No.: 15/579,030

(22) PCT Filed: May 31, 2016

(86) PCT No.: PCT/EP2016/062281
§ 371 (c)(1),
(2) Date: Dec. 1, 2017

(87) PCT Pub. No.: WO2016/193267
PCT Pub. Date: Dec. 8, 2016

(65) Prior Publication Data
US 2019/0082687 A1    Mar. 21, 2019

(30) Foreign Application Priority Data
Jun. 2, 2015 (GB) .................................... 15170251

(51) Int. Cl.
| | | |
|---|---|---|
| A01N 43/40 | (2006.01) | |
| A01N 37/40 | (2006.01) | |
| A01N 43/54 | (2006.01) | |
| A01N 43/60 | (2006.01) | |
| A01N 43/66 | (2006.01) | |
| A01N 43/78 | (2006.01) | |
| A01N 43/82 | (2006.01) | |
| C07D 241/18 | (2006.01) | |
| C07D 239/34 | (2006.01) | |
| C07D 277/34 | (2006.01) | |
| C07D 251/22 | (2006.01) | |

(52) U.S. Cl.
CPC .............. *A01N 37/40* (2013.01); *A01N 43/40* (2013.01); *A01N 43/54* (2013.01); *A01N 43/60* (2013.01); *A01N 43/66* (2013.01); *A01N 43/78* (2013.01); *A01N 43/82* (2013.01); *C07D 239/34* (2013.01); *C07D 241/18* (2013.01); *C07D 251/22* (2013.01); *C07D 277/34* (2013.01)

(58) Field of Classification Search
None
See application file for complete search history.

(56) References Cited

U.S. PATENT DOCUMENTS

| | | | | |
|---|---|---|---|---|
| 5,057,146 A | * | 10/1991 | Anthony ................ | A01N 43/40 504/255 |
| 5,874,467 A | * | 2/1999 | Bayer .................... | A01N 37/36 514/538 |
| 2010/0166896 A1 | * | 7/2010 | Zhang .................... | A01N 27/00 424/769 |

FOREIGN PATENT DOCUMENTS

| | | | | |
|---|---|---|---|---|
| EP | 0242081 A1 | 10/1987 | | |
| EP | 0256667 A2 | 2/1988 | | |
| WO | 199007493 A1 | 7/1990 | | |
| WO | 199218487 A1 | 10/1992 | | |
| WO | 199505368 A1 | 2/1995 | | |
| WO | 199521153 A1 | 8/1995 | | |
| WO | WO-9521153 A1 | * 8/1995 | ............ | A01N 37/36 |
| WO | 199902150 A1 | 1/1999 | | |
| WO | 200137662 A1 | 5/2001 | | |
| WO | 2007036710 A2 | 4/2007 | | |

OTHER PUBLICATIONS

European Search Report EP 15170251 dated Oct. 20, 2015.
Ian H. Aspinall and Paul A. Worthington, "beta-Methoxyacrylates; Synthesis of new types of strobilurin fugnicides with extended side chains", Pestic Sci ence, vol. 55, No. 2, pp. 197-198, 1999, XP-002744445, Extended summaries 9th International Congress of Pesticide Chemistry.
International Search Report for International Patent Application No. PCT/EP2016/062281 dated Sep. 27, 2016.

* cited by examiner

*Primary Examiner* — Gigi G Huang
(74) *Attorney, Agent, or Firm* — BakerHostetler; Toni-Junell Herbert

(57) ABSTRACT

The present inventions concerns use of a certain methoxyacrylate compound to control mosquitoes, and vector control solutions comprising a defined methoxyacrylate compound, in particular the invention relates to a substrate, to a composition, for controlling mosquitoes comprising a defined methoxyacrylate compound, and to certain methoxyacrylate compounds.

7 Claims, No Drawings

MOSQUITO VECTOR CONTROL COMPOSITIONS, METHODS AND PRODUCTS UTILIZING SAME

RELATED APPLICATION INFORMATION

This application is a 371 of International Application No. PCT/EP2016/062281, filed May 31, 2016 which claims priority to GB Application No. 15170251.1 filed Jun. 2, 2015, the contents of which are incorporated herein by reference herein.

The present invention is in the technical field of insect vector control, particularly mosquito control, with a certain active methoxyacrylate compound. More specifically, the present invention relates to methods of controlling mosquitoes and to substrates, products, compositions and integrated mosquito management solutions for controlling mosquitoes, each comprising the certain mosquitocidally active methoxyacrylate compound.

Mosquito control manages the population of mosquitoes to reduce their damage to human health, economies, and enjoyment. Mosquito control is a vital public-health practice throughout the world and especially in the tropics because mosquitoes spread many diseases, such as malaria (Wikipedia contributors, "Mosquito control", Wikipedia).

With the present invention, it has now been found that certain methoxyacrylate compounds are mosquitocidally active (compared to similar analogous compounds) and are surprisingly useful for controlling mosquitoes and for decreasing mosquito vector populations.

Accordingly, in a first aspect the present invention provides for the use of one or more methoxyacrylate compounds selected from Table 1 below for controlling mosquitoes.

In a second aspect, the present invention provides compositions, products, and treated articles (such as substrates or non-living materials) comprising a methoxyacrylate compound selected from the group consisting of the compounds shown in Table 1.

In a third aspect, the present invention provides integrated mosquito vector management or control solutions comprising one or more methoxyacrylate compounds selected from Table 1.

In a further aspect, a method of controlling mosquitoes, preferably mosquito vectors of pathogenic disease, which comprises contacting a mosquito or its environment with a composition comprising a mosquitocidally effective amount of a compound selected from the group consisting of from the compounds listed in Table 1, is made available.

Although certain methoxyacrylate compounds are known (see WO 90/07493, WO 92/18487, WO 95/05368, EP 0 242 081, WO 95/21153, EP 0 256 667, WO 2007/036710), the technical teaching from these documents is primarily directed to use of these compounds for control of fungi or insects on plants and crops.

Further, WO 99/02150 describes defined @3-alkoxyacrylates as being active against chloroquine-sensitive malaria pathogens, such as *Plasmodium falciparum*, and so such compounds are considered medicaments suitable for treatment or prevention of malaria directly on the individual or animal. In contrast, the present invention is directed to control of mosquitos that transmit the pathogens and viruses causing diseases by using in a vector control solution one or more of the defined list of methoxyacrylate compounds, and thereby mitigate against the individual or animal being infected/affected.

Mosquito-control operations are targeted against three different problems:
1. Nuisance mosquitoes bother people around homes or in parks and recreational areas;
2. Economically important mosquitoes reduce real estate values, adversely affect tourism and related business interests, or negatively impact livestock or poultry production;
3. Public health is the focus when mosquitoes are vectors, or transmitters, of infectious disease.

Many infectious diseases (e.g. malaria, dengue and yellow fever, lymphatic filariasis, and leishmaniasis) that are responsible for debilitating or even killing humans and animals in many countries, especially in tropical countries, are transmitted by insect vectors. For example, the mosquito parasite, *Plasmodium falciparum*, accounts for greater than 25 percent of childhood mortality outside the neonatal period. In certain parts of Africa, malaria has been ranked first by the World Bank in terms of disability-adjusted life-years lost. A number of drugs are available to treat and/or prevent some insect-borne diseases. However, not all diseases transmitted by mosquitoes can be treated efficiently. For example, there is currently no chemotherapeutic drug or vaccine available against the Dengue virus. Furthermore, in the case of antimalarial drugs, treatment with the drugs currently available is becoming less effective due to increased resistance in some *Plasmodium* strains. *Plasmodium* enters the human bloodstream as a consequence of the insect bite and causes malaria. Therefore, one of the most effective ways to prevent mosquito vector-borne illnesses is by decreasing mosquito populations in areas of high pathogen transmission and/or preventing mosquito bites in the first place. More recently, efforts have been concentrated on controlling the transmitting mosquitoes.

The three medically important genera of insects which transmit diseases are the mosquitoes *Anopheles*, *Culex* and *Aedes*. The genera *Culex* and *Aedes* belong to the sub-family Culicinae, while the *Anopheles* belongs to the sub-family Anophelinae.

Examples of diseases or pathogens transferred by the key mosquitoes are:
  *Anopheles*: malaria, filariasis;
  *Culex*: Japanese encephalitis, other viral diseases, filariasis; and
  *Aedes*: yellow fever, dengue fever, chikungunya, other viral diseases (e.g Zika virus), and filariasis;

In an attempt to reduce the problems associated with disease-transmitting mosquitoes, a wide range of insecticides and insect repellents have been developed. Mosquitoes can be targeted with insecticides when they are in a larval state or once they have developed into adults. Accordingly, insecticides which are used to kill larvae are termed larvicides whereas insecticides that are used to specifically target adult insects are called adulticides. Most of the insecticides commonly used to prevent the spread of disease are targeted against the adult mosquito and in particular against the female adult mosquito.

The organochlorine DDT was the most widespread compound used worldwide as an adulticide until it was withdrawn from use in most areas. After that, organophosphates such as malathion, carbamates and propoxur were widely used in vector control programmes in most parts of the world and were steadily replaced by pyrethroids, which became the mostly used adulticide, Organophosphates, such as pirimiphos-methyl are now being used again due to the development of pyrethroid resistance in many important vector species.

One of the most important problems associated with pyrethroids, like their predecessors, is that resistance has already developed in many insect species in several parts of the world. Pyrethroid resistance, caused either by specific detoxification enzymes or an altered target site mechanism (kdr-type mutations in the sodium channels), has been reported in most continents in the majority of medically important mosquitoes species, such as *Anopheles gambiae* in Africa and *Aedes aegypti* in Asia. If resistance continues to develop and spread at the current rate, it may render such insecticides ineffective in their current form in the not too distant future. Such a scenario would have potentially devastating consequences in public health terms, since there are as yet no obvious alternatives to many of the uses of pyrethroids.

Therefore, there is an ongoing search for insecticides for control of mosquitoes, especially for mosquitoes having developed resistance, such as against pyrethroids.

The methoxyacrylate compounds useful in the methods and other aspects of the invention are listed in Table 1 below:

TABLE 1 methoxyacrylate compounds of the invention

| Compound no. | |
|---|---|
| 1 | 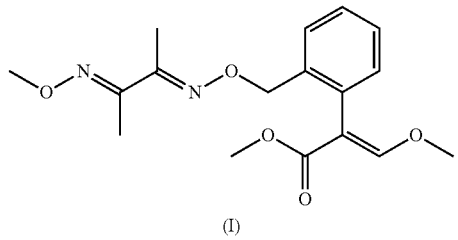 (I) |
| 2 | 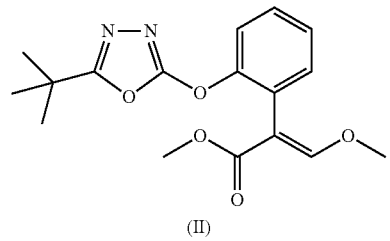 (II) |
| 3 | 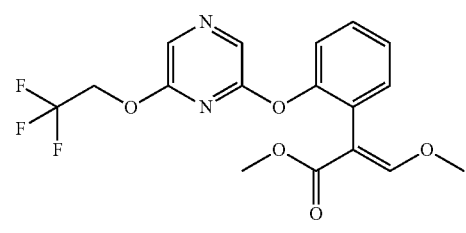 (III) |
| 4 | 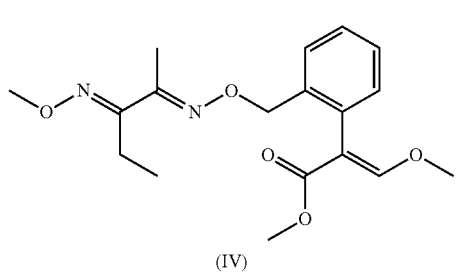 (IV) |

TABLE 1-continued methoxyacrylate compounds of the invention

| Compound no. | |
|---|---|
| 5 | 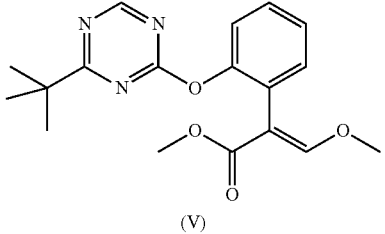 (V) |
| 6 | 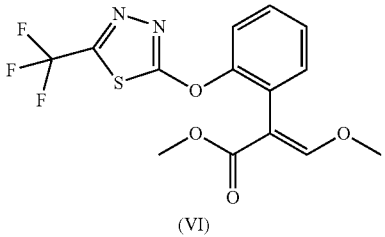 (VI) |
| 7 | 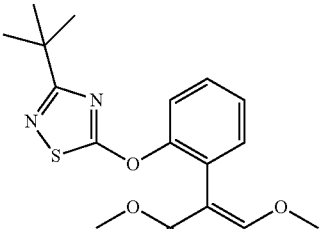 (VII) |
| 8 | 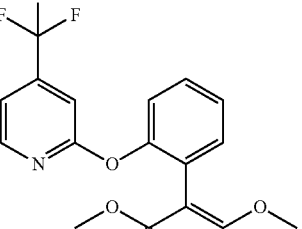 (VIII) |
| 9 | 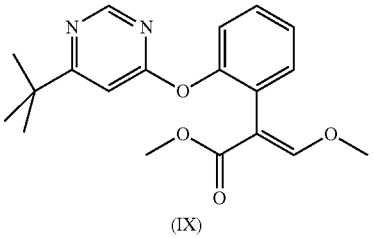 (IX) |

TABLE 1-continued
methoxyacrylate compounds of the invention
| Compound no. | |
|---|---|
| 10 | 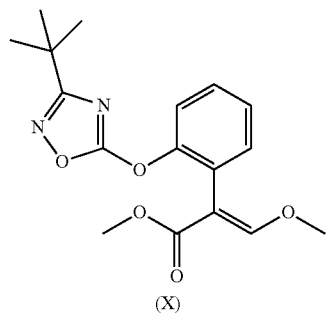 (X) |
| 11 | 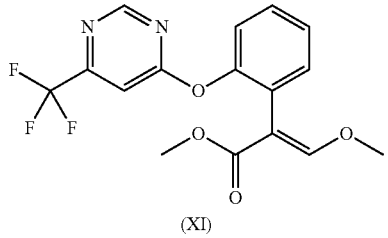 (XI) |
| 12 | 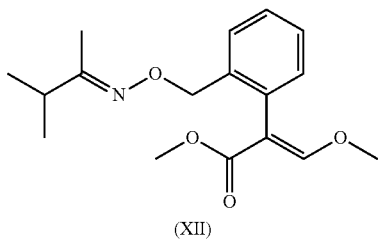 (XII) |
| 13 | 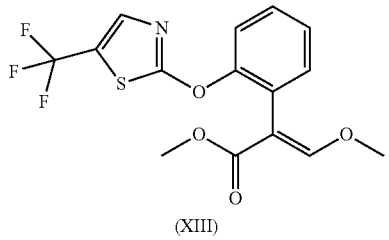 (XIII) |
| 14 | 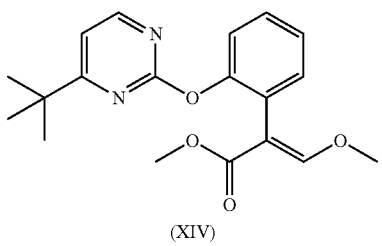 (XIV) |
| 15 | 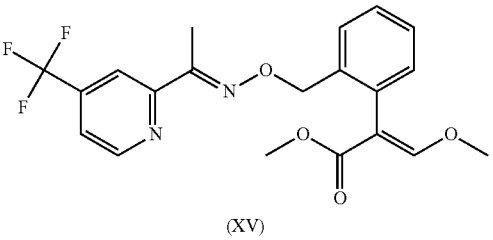 (XV) |
| 16 | 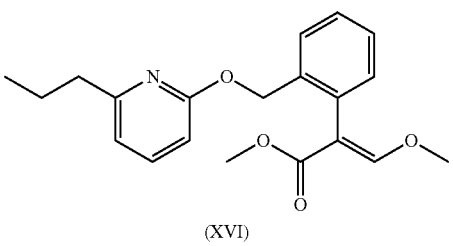 (XVI) |
| 17 | 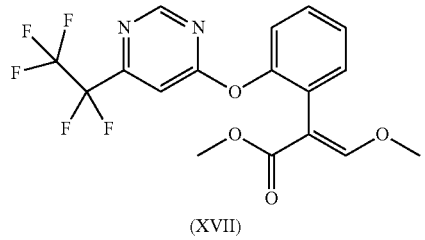 (XVII) |
| 18 | 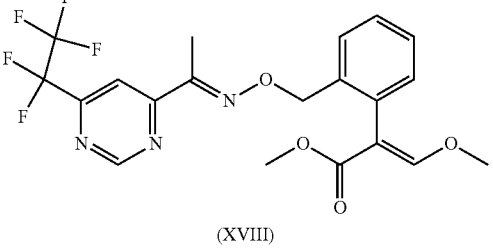 (XVIII) |
| 19 | 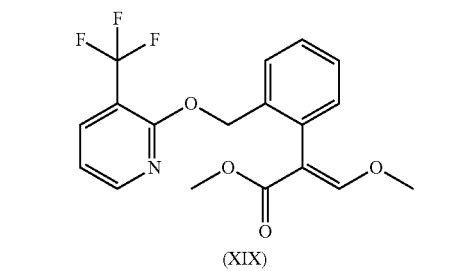 (XIX) |

TABLE 1-continued methoxyacrylate compounds of the invention

| Compound no. | |
|---|---|
| 20 | 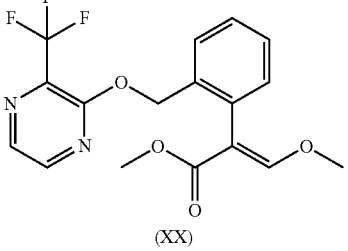 (XX) |
| 21 | 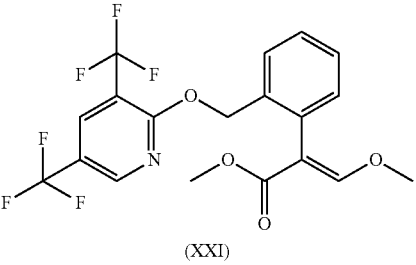 (XXI) |
| 22 | 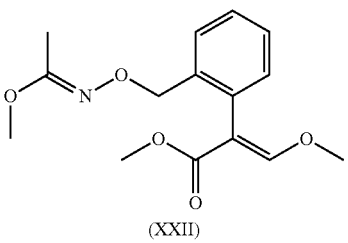 (XXII) |
| 23 | 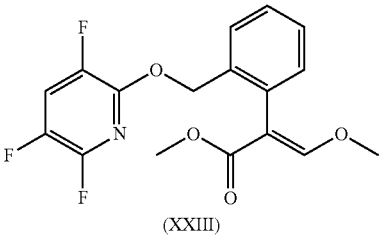 (XXIII) |

As well as the biological efficacy of the compounds of the present invention against mosquitos and resistant strains of such mosquitos, other considerations for selecting a suitable compound could include its safety (such as its toxicity, persistence) to the environment, including to the users of a vector control solution; its suitability for making a vector control solution product (whether indoor residual spray formulation, mosquito net, or another type), its suitability for adherence and availability on a surface over a period of time (in the event the solution is an indoor residual spray), and also its suitability for incorporation into a polymer product (such as a net) so that the compound would be readily available to control mosquitos on the surface of the net over a period of time and the nets can withstand multiple washings.

In an embodiment of each aspect of the present invention involving a vector control solution, the development of vector-borne diseases may be reduced by the mosquito control.

In an embodiment of each aspect of the present invention involving a vector control solution, compounds 1 to 15, 17, 18, 22 and 23 are preferred. In a further embodiment, compounds 1, 2, 4, 5, 6, 7, 8, 9, 10, 11, 12, 13, 15, 18, and 22 are preferred. Especially preferred are compounds 4, 5, 6, 7, 8, 10, 12, 13 and 22. Advantageously preferred are compounds 7, 8, and 13.

In a further aspect, the present invention make available a methoxyacrylate compound selected from the group consisting of compounds 3, 5, 9, 11, 13, 14, 16, 17, 19, 20, 21 and 23; preferably, the compound is selected from the group of compounds 3, 5, 9, 11, 13, 14, 17 and 23, especially preferred are compounds 5 and 13, The methoxyacrylate compounds useful in the methods and other aspects of the invention can be prepared similar to known procedures.

The oxime compounds (e.g. compounds 1, 4, 12, 15, 18, 22) can be prepared analogously to procedures published in WO 9007493, WO 9218487 or Pesticide Science 1999, 55(2), 197-198. The key step is the reaction of an oxime with a benzylic compound containing a leaving group LG 1 under basic conditions. LG 1 can be a halogen, preferably bromine or chlorine. The base can be an inorganic salt, preferably $Na_2CO_3$, $K_2CO_3$, $Cs_2CO_3$ or NaH. The reaction can be carried out neat or in a solvent. Preferably the reaction is carried out in a solvent. The solvent can be MeOH, EtOAc, toluene, pentane, hexane, heptane, acetone, THE (tetrahydrofuran), NMP (N-methyl-2-pyrrolidon) or DMF (N,N-dimethylformamide). The substituent R in the oxime might be a C1-C6 alkyl group, a C1-C6 alkoxy group, a N-C1-C6-alkyl amino group, N-C1-C6-alkoxy-1-C1-C4-alkylimine or an optionally substituted heterocycle (Scheme 1).

Scheme 1

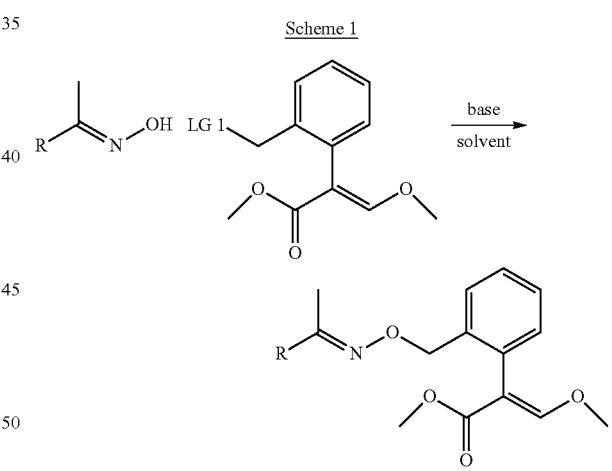

Alternatively N-hydoxy-phthalimide can be reacted with a benzylic compound containing a leaving group LG1 under basic conditions. LG 1 can be a halogen, preferably bromine or chlorine. The base can be an inorganic salt, preferably $Na_2CO_3$, $K_2CO_3$, $Cs_2CO_3$, or NaH or $Et_3N$. The reaction can be carried out neat or in a solvent. Preferably the reaction is carried out in a solvent. The solvent can be MeOH, EtOAc, toluene, pentane, hexane, heptane, acetone, THE (tetrahydrofuran), NMP (N-methyl-2-pyrrolidon) or DMF (N,N-dimethylformamide). The resulting product is treated with hydrazine hydrate in methanol in order to liberate the amino functionality. The resulting product can then react with a ketone or an imine in a solvent such as water, MeOH, EtOAc, toluene, pentane, hexane, heptane, acetone, THF (tetrahydrofuran), NMP (N-methyl-2-pyrrolidon) or DMF (N,N-dimethylformamide), preferably a mixture of water and MeOH. It might be advantageous to add a base such Et₃N or pyridine. The substituent R in the ketone or in the imine might be a C1-C6 alkyl group, a C1-C6 alkoxy group, a N-C1-C6-alkyl amino group, N-C1-C6-alkoxy-1-C1-C4-alkylimine or an optionally substituted heterocycle. The substituent R' in the amine might be hydrogen, alkyl or optionally substituted phenyl (Scheme 2).

-continued

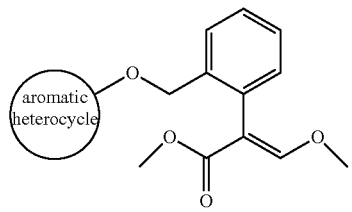

Scheme 2

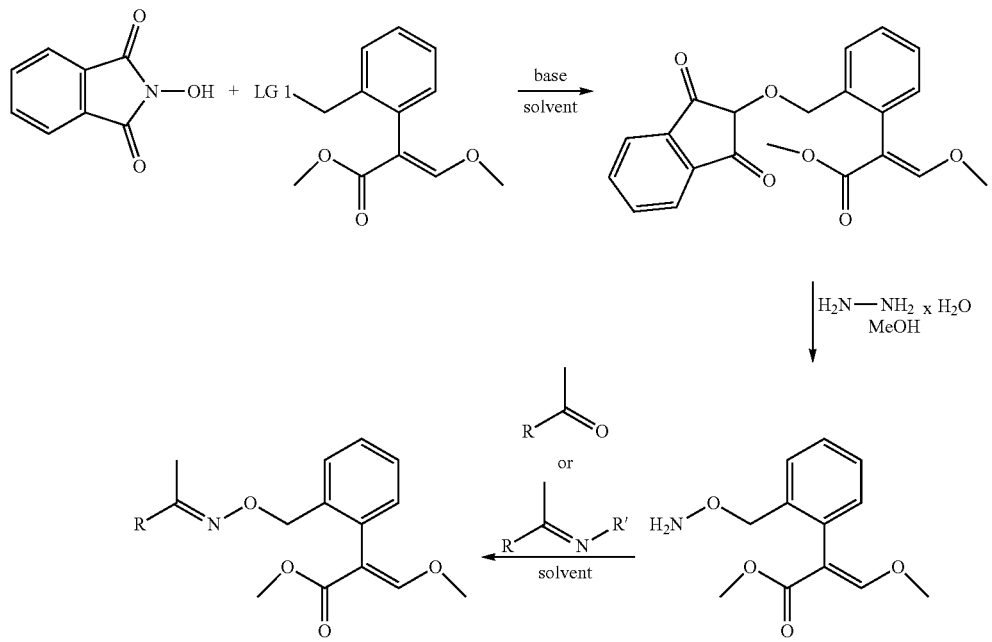

Other methoxyacrylate compounds (such as compounds 16, 19, 20, 21, 23) can be prepared by reacting an aromatic 5- or 6-membered heterocyclic compound containing a hydroxy group with a benzylic compound containing a leaving group LG1 under basic conditions. LG 1 can be a halogen, preferably bromine or chlorine. The base can be an inorganic salt, preferably Ag₂CO₃, Na₂CO₃, K₂CO₃, Cs₂CO₃ or NaH, most preferably Ag₂CO₃. The reaction can be carried out neat or in a solvent. Preferably the reaction is carried out in a solvent. The solvent can be MeOH, EtOAc, toluene, benzene, pentane, hexane, heptane, acetone, THF, NMP or DMF, preferably pentane, hexane or heptane (Scheme 3).

Alternatively an aromatic 5- or 6-membered heterocyclic compound containing a leaving group LG 2 can be reacted under basic conditions with a benzylic alcohol containing a leaving group LG 3 in ortho-position. LG 3 can be a halogen, preferably iodine, bromine, chlorine. LG 2 can be a halogen, preferably bromine, chlorine or fluorine or an alkyl sulfonyl group, preferably methylsulfonyl or an arylsulfonyl group, preferably phenylsulfonyl or tosyl. The base can be for example Na₂CO₃, K₂CO₃, Cs₂CO₃, NaH, NaOMe. The solvent can be MeOH, EtOAc, toluene, benzene, pentane, hexane, heptane, acetone, THF, NMP or DMF. In a second step the methoxyacrylate can be introduced by a palladium catalyzed cross coupling reaction. LG 4 can be a boronic acid derivitave, e.g. B(OH)₂, or metallic group, e.g. Mg—Br or ZnI or SnBu₄. The Pd catalyst can be for example Pd(PPh₄), Pd(OAc)₂+PPh₄ (Scheme 4).

Scheme 3

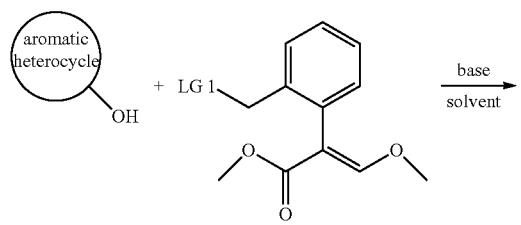

Scheme 4

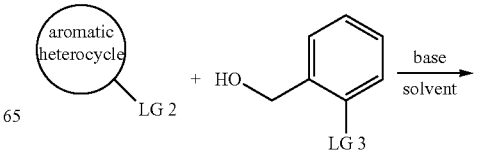

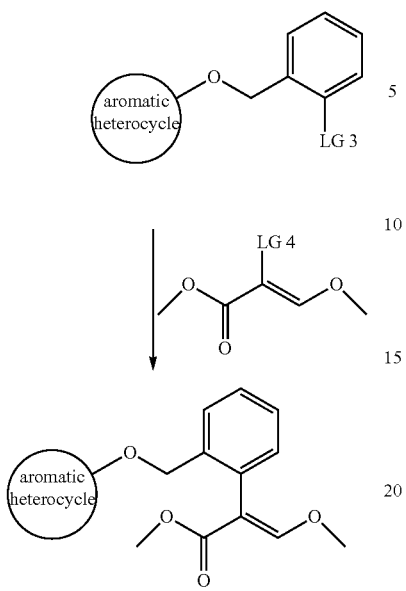

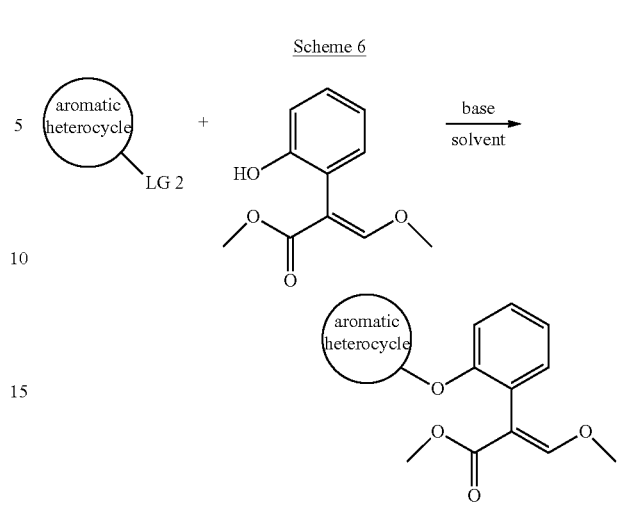

Alternatively an aromatic 5- or 6-membered heterocyclic compound containing a leaving group LG 2 can be reacted under basic conditions with a phenol containing a leaving group LG 3 in ortho-position. LG 3 can be a halogen, preferably iodine, bromine, chlorine. LG 2 can be a halogen, preferably bromine, chlorine or fluorine or an alkyl sulfonyl group, preferably methylsulfonyl or an arylsulfonyl group, preferably phenylsulfonyl or tosyl. The base can be for example $Na_2CO_3$, $K_2CO_3$, $Cs_2CO_3$, NaH, NaOMe. The solvent can be MeOH, EtOAc, toluene, benzene, pentane, hexane, heptane, acetone, THF, NMP or DMF. In a second step the methoxyacrylate can be introduced by a palladium catalyzed cross coupling reaction. LG 4 can be can be a boronic acid derivitave, e.g. $B(OH)_2$, or metallic group, e.g. Mg—Br or Znl or $SnBu_4$. The Pd catalyst can be for example $Pd(PPh_4)$, $Pd(OAc)_2+PPh_4$ (Scheme 7).

Alternatively the palladium catalyzed cross coupling reaction can be conducted in a similar way having the groups LG 3 and LG 4 reversed. LG 3 can be a halogen, preferably iodine, bromine, chlorine. LG 4 can be a boronic acid derivitave, e.g. $B(OH)_2$, or metallic group, e.g. Mg—Br or Znl or $SnBu_4$. The Pd catalyst can be for example $Pd(PPh_4)$, $Pd(OAc)_2+PPh_4$ (Scheme 5).

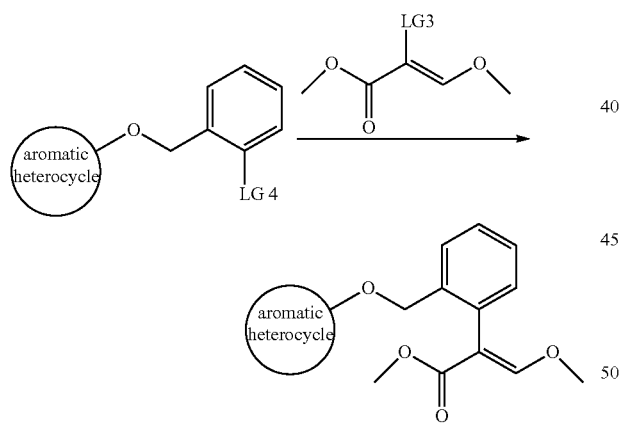

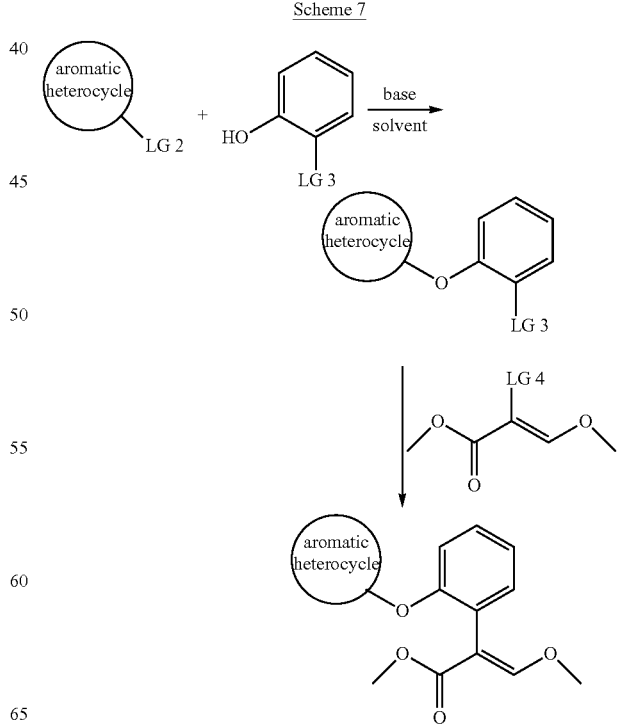

Certain methoxyacrylate compounds of this invention (e.g. compounds 2, 3, 5, 6, 7, 8, 9, 10, 11, 13, 14, 17) can be prepared according to WO 9505368 or EP 242081. In the key step an aromatic 5- or 6-membered heterocyclic compound containing a leaving group LG 2 can be reacted under basic conditions with a phenol containing a methoxyacrylate in ortho-position. LG 2 can be a halogen, preferably bromine, chlorine or fluorine or an alkyl sulfonyl group, preferably methylsulfonyl or an arylsulfonyl group, preferably phenylsulfonyl or tosyl. The base can be for example $Na_2CO_3$, $K_2CO_3$, $Cs_2CO_3$, NaH, NaOMe. The solvent can be MeOH, EtOAc, toluene, benzene, pentane, hexane, heptane, acetone, THF, NMP or DMF (Scheme 6).

Alternatively the palladium catalyzed cross coupling reaction can be conducted in a similar way having the groups LG 3 and LG 4 reversed. LG 3 can be a halogen, preferably iodine, bromine, chlorine. LG 4 can be a boronic acid derivitave, e.g. B(OH)$_2$, or metallic group, e.g. Mg—Br or ZnI or SnBu$_4$. The Pd catalyst can be for example Pd(PPh$_4$), Pd(OAc)$_2$+PPh$_4$ (Scheme 8).

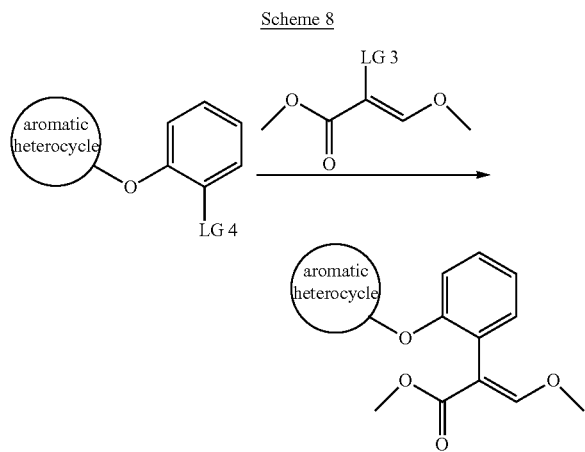

Scheme 8

Mosquito vector control is any method to limit or eradicate mosquito species which transmit disease pathogens. The most frequent types of mosquito vector control employ a variety of strategies.

Mosquito vector control focuses on utilizing preventative methods to control or eliminate mosquito populations. Common preventative measures are

- habitat control—removing or reducing areas where mosquitoes can easily breed can help limit population growth. For example, stagnant water removal, destruction of old tires and cans which serve as mosquito breeding environments and good management of stored water can reduce areas of excessive mosquito incidence.
- reducing contact—limiting exposure to mosquitoes can reduce infection risks significantly. For example, bed nets, window screens on homes, or protective clothing can help reduce the likelihood contact with mosquitoes. To be effective this requires education and promotion of methods among the population to raise the awareness of mosquito threats.
- chemical control—insecticides, larvicides, and repellents can be used to control mosquitoes. For example, larvicides can be used in mosquito breeding zones; insecticides can be applied to house walls or bed nets, and use of personal repellents can reduce incidence of mosquitoes bites and thus infection. The use of pesticides for mosquito vector control is promoted by the World Health Organization (WHO) and has proven to be highly effective.
- biological control—the use of natural mosquito vector predators, such as bacterial toxins or botanical compounds, can help control mosquito populations. Using fish that eat mosquito larvae, has been demonstraited to have some success.
- population control through the release of sterilized, or genetically modified, male mosquitoes has also been shown to control mosquito vector populations and reduce infection risks.

A number of considerations is taken into account when determining which methoxyacrylate compound would be suitable for use in a particular mosquito vector control strategy, such as favourable safety profile, biological performance and affordability.

In one embodiment, the methoxyacrylate compounds shown in Table 1 in accordance with the methods and other aspects of the present invention are useful in controlling mosquitoes, in particular mosquitoes selected from the genus *Anopheles, Culex* and *Aedes*. Examples include *Aedes aegypti, Aedes albopictus, Aedes japonicas, Aedes vexans, Coquillettidia perturbans, Culex molestus, Culex pallens, Culex pipiens, Culex quinquefasciatus, Culex restuans, Culex tarsalis, Anopheles albimanus, Anopheles albitarsis, Anopheles annularis, Anopheles aquasalis, Anopheles arabiensis, Anopheles aconitus, Anopheles atroparvus, Anopheles balabacensis, Anopheles coluzzii, Anopheles culicifacies, Anopheles darlingi, Anopheles dirus, Anopheles farauti, Anopheles flavirostris, Anopheles fluviatilis, Anopheles freeborni, Anopheles funestus, Anopheles gambiae* s.l., *Anopheles koliensis, Anopheles* labranchiae, *Anopheles lesteri, Anopheles leucosphyrus, Anopheles maculatus, Anopheles marajoara, Anopheles melas, Anopheles merus, Anopheles messeae, Anopheles minimus, Anopheles moucheti, Anopheles nili, Anopheles nuneztovari, Anopheles plumbeus, Anopheles pseudopunctipennis, Anopheles punctipennis, Anopheles punctulatus, Anopheles quadrimaculatus, Anopheles sacharovi, Anopheles sergentii, Anopheles sinensis, Anopheles stephensi, Anopheles subpictus, Anopheles sundaicus, Anopheles superpictus*, and *Mansonia titillans*, Ochlerotatus stimulans, Ochlerotatus japonicas (each of which is an example of a mosquito capable of carrying or vectoring a pathogenic disease).

By control is meant that a methoxyacrylate compound useful in the methods and other aspects of the invention is employed in a manner that kills or repels the mosquito such that biting does not occur or in a manner that decreases mosquito populations such that biting does not occur as frequently.

In an embodiment, the methoxyacrylate compound selected from the group consisting of 4, 5, 6, 7, 8, 10, 12, 13 and 22 is useful in controlling one or more mosquitos selected from the genus *Anopheles, Culex* and *Aedes*, in particular one or more of *Aedes aegypti, Aedes albopictus, Aedes japonicas, Aedes vexans, Culex molestus, Culex pallens, Culex pipiens, Culex quinquefasciatus, Culex restuans, Culex tarsalis, Anopheles albimanus, Anopheles arabiensis, Anopheles coluzzii, Anopheles darlingi, Anopheles dirus, Anopheles funestus, Anopheles gambiae* s.l., *Anopheles melas, Anopheles minimus, Anopheles sinensis, Anopheles stephensi, Mansonia titillans*.

In an embodiment, the methoxyacrylate compounds of Table 1 are useful in the methods and other aspects of the invention to control adult mosquitoes.

In another embodiment each of the methoxyacrylate compound 4, 5, 6, 7, 8, 10, 12, 13 and 22 is especially useful in controlling one or more of the mosquitoes listed in table 2 below:

| Compound no. | Mosquito species | Compound no. | Mosquito species |
|---|---|---|---|
| 4 | *Aedes aegypti* | 5 | *Aedes aegypti* |
| 4 | *Anopheles funestus* | 5 | *Anopheles funestus* |
| 4 | *Anopheles gambiae* s.l. | 5 | *Anopheles gambiae* s.l. |

| Compound no. | Mosquito species | Compound no. | Mosquito species |
| --- | --- | --- | --- |
| 4 | Anopheles stephensi | 5 | Anopheles stephensi |
| 4 | Anopheles arabiensis | 5 | Anopheles arabiensis |
| 4 | Aedes albopictus | 5 | Aedes albopictus |
| 4 | Anopheles coluzzii | 5 | Anopheles coluzzii |
| 6 | Aedes aegypti | 7 | Aedes aegypti |
| 6 | Anopheles funestus | 7 | Anopheles funestus |
| 6 | Anopheles gambiae s.l. | 7 | Anopheles gambiae s.l. |
| 6 | Anopheles stephensi | 7 | Anopheles stephensi |
| 6 | Anopheles arabiensis | 7 | Anopheles arabiensis |
| 6 | Aedes albopictus | 7 | Aedes albopictus |
| 6 | Anopheles coluzzii | 7 | Anopheles coluzzii |
| 8 | Aedes aegypti | 10 | Aedes aegypti |
| 8 | Anopheles funestus | 10 | Anopheles funestus |
| 8 | Anopheles gambiae s.l. | 10 | Anopheles gambiae s.l. |
| 8 | Anopheles stephensi | 10 | Anopheles stephensi |
| 8 | Anopheles arabiensis | 10 | Anopheles arabiensis |
| 8 | Aedes albopictus | 10 | Aedes albopictus |
| 8 | Anopheles coluzzii | 10 | Anopheles coluzzii |
| 12 | Aedes aegypti | 13 | Aedes aegypti |
| 12 | Anopheles funestus | 13 | Anopheles funestus |
| 12 | Anopheles gambiae s.l. | 13 | Anopheles gambiae s.l. |
| 12 | Anopheles stephensi | 13 | Anopheles stephensi |
| 12 | Anopheles arabiensis | 13 | Anopheles arabiensis |
| 12 | Aedes albopictus | 13 | Aedes albopictus |
| 12 | Anopheles coluzzii | 13 | Anopheles coluzzii |
| 22 | Aedes aegypti | | |
| 22 | Anopheles funestus | | |
| 22 | Anopheles gambiae s.l. | | |
| 22 | Anopheles stephensi | | |
| 22 | Anopheles arabiensis | | |
| 22 | Aedes albopictus | | |
| 22 | Anopheles coluzzii | | |

Insecticide resistant mosquito species have also been detected and accordingly in an embodiment, a methoxyacrylate compound useful in the methods and other aspects of the invention is suitable for controlling insecticide-resistant mosquitoes, such as pyrethroid and/or carbamate-resistant mosquitoes.

Pyrethroids are the only insecticides that have obtained WHO recommendation against Malaria vectors on both Indoor Residuals Sprays (IRS) and Long Lasting Insecticidal Mosquito Nets (LLINs), in the form of Alpha-Cypermethrin, Bifenthrin, Cyfluthrin, Permethrin, Deltamethrin, Lambda-Cyhalothrin and Etofenprox. It has been the chemical class of choice in agriculture and public health applications over the last several decades because of its relatively low toxicity to humans, rapid knock-down effect, relative longevity (duration of 3-6 months when used as IRS), and low cost.

However, massive use of pyrethroids in agricultural applications and for vector control led to the development of resistance in major malaria and dengue vectors. Strong resistance has e.g. been reported for the pyrethroid Deltamethrin (and Permethrin) for the *Anopheles gambiae* Tiassalé (from southern Cote d'Ivoire) strain (Constant V.A. Edi et al., Emerging Infectious Diseases; Vol. 18, No. 9, September 2012). Pyrethroid resistance was also reported for Permethrin, Deltamethrin and Lambda-Cyhalothrin for the *Aedes aegypti* Cayman Island strain (Angela F. Harris et al., Am. J. Trop. Med. Hyg., 83(2), 2010) and Alpha-Cypermethrin, Permethrin and Lambda-Cyhalothrin for certain *Anopheles* strains (Win Van Bortel, Malaria Journal, 2008, 7:102).

In another embodiment of the invention, the methoxyacrylate compounds of Table 1 can be suitable for use against insecticide-resistant mosquitoes that are selected from *Anopheles gambiae* RSPH, *Anopheles gambiae* Tiassale, *Anopheles gambiae* Akron, *Anopheles gambiae* Kisumi Rdl, *Anopheles arabiensis* NDjamina, *Anopheles coluzzii* VK7, *Anopheles funestus* FUMOZ, *Aedes aegypti* Grand Cayman and *Culex quinquefasciatus* strain POO.

*Anopheles gambiae*, strain RSPH is a multi-resistant mosquito (target-site and metabolic-resistance) that is described in the reagent catalog of the Malaria Research and Reference Reagent Resource Center (www.MR4.org; MR4-number: MRA-334).

*Anopheles gambiae*, strain Tiassale is a multi-resistant mosquito (target and metabolic-resistant strain) which shows cross-resistance between carbamates, organophosphates and pyrethroids and is described in Constant V.A. Edi et al., Emerging Infectious Diseases; Vol. 18, No. 9, September 2012 and Ludovic P Ahoua Alou et al., Malaria Journal 9: 167, 2010).

*Anopheles gambiae*, strain Akron is a multi-resistant mosquito (target and metabolic-resistant strain) and is described in Djouaka F Rousseau et al., BMC Genomics, 9:538; 2008.

*Anopheles coluzzii*, strain VK7 is a target-resistant mosquito and is described in Dabire Roch Kounbobr et al., Malaria Journal, 7: 188, 2008.

*Anopheles funestus*, strain FUMOZ is a metabolic-resistant strain and is described in Hunt et al., Med Vet Entomol. 2005 September; 19(3):271-5). In this article it has been reported that *Anopheles funestus*—as one of the major malaria vector mosquitoes in Africa—showed resistance to pyrethroids and carbamate insecticides in South Africa.

*Anopheles gambiae*, strain Kisumi Rdl, a dieldrin resistant strain from Kenya.

*Anopheles arabiensis*, strain NDjamina, a pyrethroid resistant from Chad.

*Aedes aegypti*, strain Grand Cayman is a target-resistant mosquito and is described in Angela F. Harris, Am. J. Tro. Med. Hyg. 83(2), 2010.

*Culex quinquefasciatus* (metabolic-resistant to DDT strain P00); received from Texchem, Penang, Malaysia.

Vector control solution are means to control a vector, such as a mosquito. Examples of such means are compositions, products, and treated articles, which include a substrate or non-living material incorporating (e.g. coated or impregnated with) a methoxyacrylate compound of Table 1, spray products (e.g. indoor sprays, and aerosol products) comprising a methoxyacrylate compound of Table 1, paint compositions comprising a methoxyacrylate compound of Table 1, and products or treated articles comprising a methoxyacrylate compound of Table 1.

Examples of integrated mosquito vector management or control solutions of the invention, such as solutions for controlling mosquito bites or decreasing relevant mosquito populations, include the use of such compositions, products, treated articles and substrates of the invention at a locus of potential or known interaction between the mosquito vector and an animal, including a human, that is susceptible to a pathogenic disease infection transmitted by such vector. Suitable integrated solutions within the scope of the present invention also include identifying mosquito breeding sites and positioning compositions, products, treated articles and substrates of the invention at such sites.

Examples of a substrate or non-living material of the invention are self-supporting film/sheet (e.g., screens), threads, fibres, yarns, pellets, weaves (or textiles (e.g. for clothing)), nets, tents, and curtains incorporating (e.g. coated or impregnated with) a methoxyacrylate compound of Table 1, which can be used to protect against mosquito bites. In particular, it is well known that humans can be protected in their sleep from mosquito stings by insecticidally coated sleeping nets. Coated or impregnated weaves of the invention can also be used as curtains in front of windows, doors open eaves, or ventilation openings, in order to control mosquito entering dwellings.

The use of a compound in a substrate of the present invention (e.g. nets and weaves) achieves at least one of the following objects:
 good insecticidal effect
 fast-acting insecticidal efficacy
 long-lasting insecticidal efficacy
 uniform release of active ingredient
 long durability (including resisting multiple washings over an extended period)
 simple production
 safe to the user The nets and weaves (or textiles) of the invention that incorporate (e.g. are coated or impregnated with) a methoxyacrylate compound of Table 1, are made up of a variety of natural and synthetic fibres, also as textile blends in woven or non-woven form, as knit goods or fibres. Natural fibres are for example cotton, raffia, jute, flax, sisal, hessian, wool, silk or hemp. Synthetic fibres may be made of polyamides, polyesters, polyacrylonitriles, polyolefines, for example polypropylene or polyethylene, Teflon, and mixtures of fibres, for example mixtures of synthetic and natural fibres. Polyamides, polyolefins and polyesters are preferred as fibre material. Polyester, such a polyethylene terephthalate, are especially preferred. Most preferred are nettings made from polyethylene and/or polypropylene.

The art discloses methods suitable for incorporating (by way of coating) a compound onto nets and weaves (see for example, WO2003/034823, WO 2008/122287, WO 01/37662, US2009036547, WO 2007/036710), from dipping or submerging them into a formulation of the insecticide or by spraying the formulation onto their surfaces. After treating the nets and weaves of the invention, they may be dried simply at ambient temperatures (see also below for more background). Such methods are also suitable for incorporating (by way of coating) a methoxyacrylate compound of Table 1.

Also disclosed in the art are methods suitable for incorporating by way of impregnating a compound within the net or weave by making polymer material in the presence of the methoxyacrylate, which is then extruded into fibres, threads or yarns, for making the nets and weaves (see for example, WO08004711, WO2009/121580, WO2011/128380, WO2011/141260, WO2010/118743). Such nets and weaves having available at the surface of the net and weave an effective amount of the compound so as to control mosquito bites. Generally the compound is mixed with the molten polymer. Such methods are also suitable for incorporating (by way of impregnating) a methoxyacrylate compound of Table 1.

The term "incorporating" or "incorporated" in context of the compound of the invention, additives and other insecticides is meant that the substrate or non-living material comprises or contains the respectively defined compound, additive and/or insecticide, such as by coating or impregnation.

Preferably the substrate of the present invention is a net, which net is preferably a long lasting net, incorporated with a methoxyacrylate compound of Table 1 by way of coating the net with a composition comprising a methoxyacrylate compound of Table 1, or by way of making a polymeric material in the presence of such a methoxyacrylate compound and then processing the resultant polymeric material into an inventive net.

In accordance with the invention, when a methoxyacrylate compound of Table 1 is used within the polymer, then during use of the resulting net or weave made from the polymer, such methoxyacrylate compound is released to the surface of the net to control against mosquito bites-such control is sustained at adequate level and for adequate amount of time.

Examples of suitable polymers are polyamides, polyesters, polyacrylonitriles, polyolefines, such as polyethylene compositions that can be made from different polyethylene polymers; these may be LDPE, LLDPE, MDPE and HDPE. LLDPE (Linear low-density polyethylene) is a substantially linear polymer (polyethylene), with significant numbers of short branches, commonly made by copolymerization of ethylene with longer-chain olefins. MDPE is medium-density polyethylene is a substantially linear polymer of polyethylene with shorter chain length than HDPE. HDPE (High-Density PolyEthylene) or PolyEthylene High-Density (PEHD) is a polyethylene thermoplast. HDPE has little branching, giving it stronger intermolecular forces and tensile strength than lower-density polyethylene. It is also harder and more opaque and can withstand somewhat higher temperatures (120 degrees C.1 248 degrees Fahrenheit for short periods, 110 degrees centigrade/230 degrees Fahrenheit continuously). HDPE yarns are stronger than LDPE mixed polyethylene yarns. LLDPE differs structurally from conventional low-density polyethylene (LDPE) because of the absence of long chain branching. These polyethylene compositions (HDPE, LDPE, LLDPE and mixture thereof) are generally used for preparing yarns and polyethylene based textile products. Methods for incorporating an insecticide compound into the polymer without weakening its resulting properties are known in the art, such as using mixtures of HDPE and LDPE. Such methods can also be used to incorporate a methoxyacrylate compound of Table 1 into a polymer.

Examples of spray products of the present invention are indoor residual sprays or space sprays comprising a methoxyacrylate compound of Table 1. Indoor Residual Spraying (IRS) is the technique of applying a residual deposit of an insecticide onto indoor surfaces where vectors rest, such as on walls and ceilings. The primary goal of indoor residual spraying is to reduce the lifespan of the mosquito vectors and thereby reduce or interrupt disease transmission. The secondary impact is to reduce the density of mosquitos within the treatment area. IRS is a recognised, proven and cost-effective intervention method for the control of malaria and it is also used in the management of Leishmaniasis and Chagas disease. Many malaria mosquito vectors are endophilic, resting inside houses after taking a blood meal. These mosquitoes are particularly susceptible to control through indoor residual spraying (IRS) comprising a methoxyacrylate compound of Table 1. As its name implies, IRS involves coating the walls and other surfaces of a house with a residual insecticide. For several months, the methoxyacrylate compound will kill mosquitoes that come in contact with these surfaces. IRS does not directly prevent people from being bitten by mosquitoes. Rather, it usually kills mosquitoes after they have fed, if they come to rest on the sprayed surface. IRS thus prevents transmission of infection to other persons. To be effective, IRS must be applied to a very high proportion of households in an area (usually greater than 70 percent). Although the community plays a passive role in IRS programs, cooperation with an IRS effort is a key to its success. Community participation for IRS often consists of cooperating with the spray teams by removing food and covering surfaces prior to spraying and refraining from covering the treated surfaces with new paint or plaster. However, community or individual householder opposition to IRS due to the smell, mess, possible chemical exposure, or sheer bother has become a serious problem in some areas.

Therefore, sprays in accordance with the invention having good residual efficacy and acceptable odour are particularly suited as a component of integrated mosquito vector management or control solutions.

In contrast to IRS, which requires that the active methoxyacrylate compound of Table 1 is bound to surfaces of dwellings, such as walls, ceiling, space spray products of the invention rely on the production of a large number of small insecticidal droplets intended to be distributed through a volume of air over a given period of time. When these droplets impact on a target mosquito, they deliver a lethal dose of the methoxyacrylate. The traditional methods for generating a space-spray include thermal fogging (whereby a dense cloud of insecticide droplets is produced giving the appearance of a thick fog) and Ultra Low Volume (ULV), whereby droplets are produced by a cold, mechanical aerosol-generating machine.

Since large areas can be treated at any one time this method is a very effective way to rapidly reduce the population of flying mosquitoes in a specific area. Since there is very limited residual activity from the application it must be repeated at intervals of 5-7 days in order to be fully effective.

This method can be particularly effective in epidemic situations where rapid reduction in mosquito numbers is required. As such, it can be used in urban dengue control campaigns. Effective space-spraying is generally dependent upon the following specific principles:

Target insects are usually flying through the spray cloud (or are sometimes impacted whilst resting on exposed surfaces). The efficiency of contact between the spray droplets and target insects is therefore crucial. This is achieved by ensuring that spray droplets remain airborne for the optimum period of time and that they contain the right dose of insecticide. These two issues are largely addressed through optimizing the droplet size.

If droplets are too big they drop to the ground too quickly and don't penetrate vegetation or other obstacles encountered during application (limiting the effective area of application). If one of these big droplets impacts an individual insect then it is also 'overkill' since a high dose will be delivered per individual insect.

If droplets are too small then they may either not deposit on a target insect (no impaction) due to aerodynamics or they can be carried upwards into the atmosphere by convection currents.

The optimum size of droplets for space-spray application are droplets with a Volume Median Diameter (VMD) of 10-25 microns.

The compositions of the present invention may be made available in a spray product as an aerosol-based application, including aerosolized foam applications. Pressurised cans are the typical vehicle for the formation of aerosols. An aerosol propellant that is compatible with the insecticide compound is used. Preferably, a liquefied-gas type propellant is used. Suitable propellants include compressed air, carbon dioxide, butane and nitrogen. The concentration of the propellant in the methoxyacrylate composition is from about 5 percent to about 40 percent by weight of the methoxyacrylate composition, preferably from about 15 percent to about 30 percent by weight of the methoxyacrylate composition.

In one embodiment, the methoxyacrylate formulation of the invention can also include one or more foaming agents. Foaming agents that can be used include sodium laureth sulphate, cocamide DEA, and cocamidopropyl betaine. Preferably, the sodium laureth sulphate, cocamide DEA and cocamidopropyl are used in combination. The concentration of the foaming agent(s) in the methoxyacrylate composition is from about 10 percent to about 25 percent by weight, more preferably 15 percent to 20 percent by weight of the composition.

When the methoxyacrylate formulation is used in an aerosol application not containing foaming agents), the composition of the present invention can be used without the need for mixing directly prior to use. However, aerosol formulations containing the foaming agents do require mixing (i.e. shaking) immediately prior to use. In addition, if the formulations containing foaming agents are used for an extended time, they may require additional mixing at periodic intervals during use.

A dwelling area may also be treated with the methoxyacrylate composition of the present invention by using a burning formulation, such as a candle, a smoke coil or a piece of incense containing the composition. For example, composition may be comprised in household products such as "heated" air fresheners in which insecticidal compositions are released upon heating, for example, electrically, or by burning.

The compositions of the present invention containing a methoxyacrylate compound of Table 1 may be made available in a spray product as an aerosol, a mosquito coil, and/or a vaporiser or fogger.

The concentration of the methoxyacrylate compound of Table 1 in the polymeric material, fibre, yarn, weave, net, or substrate, each of the invention, can be varied within a relatively wide concentration range from, for example 0.05 to 15 percent by weight, preferably 0.2 to 10 percent by weight, more preferably 0.4 to 8 percent by weight, especially 0.5 to 5, such as 1 to 3, percent by weight.

The percentages mentioned above are based on dry weight of the net or substrate or non-living material.

Similarly, the concentration of the compound of the invention in the composition (whether for treating surfaces or for coating a fibre, yarn, net, weave) can be varied within a relatively wide concentration range from, for example 0.1 to 70 percent by weight, such as 0.5 to 50 percent by weight, preferably 1 to 40 percent by weight, more preferably 5 to 30 percent by weight, especially 10 to 20 percent by weight.

The concentration shall be chosen according to the field of application such that the requirements concerning insecticidal efficacy, durability and toxicity are met. Adapting the properties of the material can also be accomplished and so custom-tailored textile fabrics are obtainable in this way.

The methoxyacrylate compound of Table 1 when used in the IRS methods of the invention is present on a surface of a dwelling at a coverage of from 0.01 to 2 grams of AI per m2, preferably from 0.05 to 1 grams of AI per m2, especially from 0.1 to 0.7 grams of AI per m2.

Accordingly an effective amount of a methoxyacrylate compound of Table 1 can depend on its how its been used, the mosquito against which control is most desired and the environment its been used. Therefore, an effective amount of a methoxyacrylate compound of Table 1 is sufficient that control of a mosquito is achieved; in case of:

use as IRS formulation, the effective amount is such that coverage of the AI on the surface is from 0.01 to 2 grams of AI per m2, preferably from 0.05 to 1 grams of AI per m2, especially from 0.1 to 0.7 grams of AI per m2;

use incorporated within a net or substrate, the effective amount is 0.05 to 15 percent by weight, preferably 0.2 to 10 percent by weight, more preferably 0.4 to 8 percent by weight, especially 0.5 to 5, such as 1 to 3, percent by weight.

Generally the methoxyacrylate compound of Table 1 when used in certain products of the invention is continuously distributed in a thread, yarn, net or weave, but can also be partially or discontinuously distributed in a thread, yarn, net or weave. For example, a net may contain certain parts which are coated or which is made-up of impregnated fibre, and certain other parts which are not; alternatively some of the fibres making up the net is impregnated, or is coated, with the compound of the invention, and some of the other fibres not or these other fibres are impregnated, or are coated, with another insecticide compound (see below).

Nets of the invention impregnated, or coated, with a methoxyacrylate compound of Table 1 can satisfy the criteria of the WHOPES directive (see "Guidelines for laboratory and field testing of long-lasting insecticidal mosquito nets", 2005, http://www.who.int/whopes/guidelines/en/) for insecticide-containing long-lasting mosquito nets up to 20 washes only, which means that such nets should not lose their biological activity after just 20 wash cycles or so.

In an embodiment, a net of the invention impregnated, or coated, with a methoxyacrylate compound of Table 1 can have biological activity in accordance with WHOPES guidelines of a knockdown after 60 minutes of between 95 percent and 100 percent or a mortality after 24 hours of between 80 percent and 100 percent after at least 20, such as 25, preferably at least 30 and even more preferably at least 35 washes.

The "WHOPES directive" is to be understood as meaning the directive "Guidelines for laboratory and field testing of long-lasting insecticidal mosquito nets", 2005). This directive is retrievable at the following interact address: http://www.who.int/whopes/guidelines/en/.

When a net is "impregnated with" a methoxyacrylate compound of Table 1 to prepare a net of the present invention, the fibres making up the net are made by melting a polymer, a methoxyacrylate compound of Table 1 and optionally other compounds, such as other insecticides, additives, stabilisers. When a net is impregnated with such a methoxyacrylate compound, then the net of the invention contains synthetic fibres; in contrast, a net of the invention coated with such a methoxyacrylate compound contains synthetic fibres and/or natural fibres.

The polymeric materials useful in the compositions of the invention incorporating a methoxyacrylate compound of Table 1 can be produced by mixing such a methoxyacrylate compound with the polymer in the liquid phase, and optionally other additives (such as binders and/or synergists), and other insecticidal compounds.

Methods of making suitable polymeric materials and then processing it are described in the art—see for example, WO09121580, WO2011/141260.

For example, nets based on an methoxyacrylate insecticide-containing polymeric material are produced by the following steps:

a) melting the polymer to be used and one or more insecticidally active ingredients together or separately at temperatures between 120 and 250 degrees centigrade,
b) forming the melt of step a) into spun threads and cooling,
c) optionally leading the spun threads formed in step b) through a drawing system and drawing and then optionally setting out the threads,
d) knitting the spun threads to form a net,
e) subjecting the net to a heat-setting operation wherein the temperature for the heat-setting operation is chosen to be 20 degrees centigrade below the melting temperature of the polymer to be used.

The heat setting in step e) of the production of the nets is preceded by a washing step. Water and a detergent is preferably used for this. The heat setting is preferably carried out in a dry atmosphere.

Although the manufacture of the nets incorporated with the insecticide compound can occur in a single location, it is also envisaged that the different steps can take place in different locations. So a composition comprising a methoxyacrylate compound may be made which can then be processed into a polymer. Accordingly, the present invention also provides a composition comprising a methoxyacrylate compound of Table 1 in a concentrated form, which composition may also contain additives (such as binders and/or synergists), and other insecticidal compound(s) (which composition had been prepared explicitly for making a polymer material impregnated with the methoxyacrylate compound of Table 1 (such a composition is often referred to as a "masterbatch")). The amount of the methoxyacrylate compound of Table 1 in the masterbatch would depend on the circumstances, but in general can be 10 to 95 percent by weight, such as 20 to 90 percent by weight, preferably 30 to 85 percent by weight, more preferably 35 to 80 percent by weight, especially 40 to 75 percent by weight.

Also made available in the present invention are compositions or formulations for coating walls, floors and ceilings inside of buildings and for coating a substrate or non-living material, which comprise a methoxyacrylate compound of Table 1. The inventive compositions can be prepared using known techniques for the purpose in mind, which could contain a binder to facilitate the binding of the compound to the surface or other substrate. Agents useful for binding are known in the art and tend to be polymeric in form. The type of binder suitable for composition to be applied to a wall surface having particular porosities, binding characteristics would be different to a fibre, yarn, weave or net—a skilled person, based on known teachings, would select a suitable binder.

Typical binders are poly vinyl alcohol, modified starch, poly vinyl acrylate, polyacrylic, polyvinyl acetate co polymer, polyurethane, and modified vegetable oils. Suitable binders can include latex dispersions derived from a wide variety of polymers and co-polymers and combinations thereof. Suitable latexes for use as binders in the inventive compositions comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, as well as post-dispersed suspensions of silicones or polyurethanes. Also suitable may be a polytetrafluoroethylene (PTFE) polymer for binding the active ingredient to other surfaces.

The formulation according to the present invention comprises at least one compound listed in Table 1 (or a pesticide (A)), and a carrier, such as water (C), and optionally a polymeric binder (B) and further components (D).

The polymeric binder binds the methoxyacrylate compounds to the surface of the non-living material and ensures a long-term effect. Using the binder reduces the elimination of the methoxyacrylate pesticide out of the non-living material due to environmental effects such as rain or due to human impact on the non-living material such as washing and/or cleaning it. The further components can be an additional insecticide compound, a synergist, a UV stabiliser.

The inventive compositions can be in a number of different forms or formulation types, such as suspensions, capsules suspensions, and a person skilled in the art can prepare the relevant composition based on the properties of the methoxyacrylate compound, its uses and also application type.

For example, the methoxyacrylate compounds used in the methods and other aspects of the present invention may be encapsulated in the formulation. A encapsulated compound can provide improved wash-fastness and also longer period of activity. The formulation can be organic based or aqueous based, preferably aqueous based.

Microencapsulated methoxyacrylate compounds suitable for use in the compositions and methods according to the invention are prepared with any suitable technique known in the art. For example, various processes for microencapsulating material have been previously developed. These processes can be divided into three categories-physical methods, phase separation and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles. The concentration of the methoxyacrylate compound present in the microcapsules can vary from 0.1 to 60% by weight of the microcapsule.

The formulation according to the invention may be formed by mixing all ingredients together with water optionally using suitable mixing and/or dispersing aggregates. In general, the formulation is formed at a temperature of from 10 to 70 degrees centigrade, preferably 15 to 50 degrees centigrade, more preferably 20 to 40 degrees centigrade.

It is possible to use a pesticide (A), solid polymer (B) and optionally additional additives (D) and to disperse them in the aqueous component (C).

If a binder is present in a composition of the present invention, it is preferred to use dispersions of the polymeric binder (B) in water as well as aqueous formulations of the pesticide (A) in water which have been separately prepared before. Such separate formulations may contain additional additives for stabilizing (A) and/or (B) in the respective formulations and are commercially available. In a second process step, such raw formulations and optionally additional water (component (C)) are added.

Also combinations are possible, i.e. using a pre-formed dispersion of (A) and/or (B) and mixing it with solid (A) and/or (B).

A dispersion of the polymeric binder (B) may be a pre-manufactured dispersion already made by a chemicals manufacturer.

However, it is also within the scope of the present invention to use "hand-made" dispersions, i.e. dispersions made in small-scale by an end-user. Such dispersions may be made by providing a mixture of about 20 percent of the binder (B) in water, heating the mixture to temperature of 90 to 100 degrees centigrade and intensively stirring the mixture for several hours.

It is possible to manufacture the formulation as a final product so that it can be readily used by the end-user for the process according to the present invention. However, it is of course also possible to manufacture a concentrate, which may be diluted by the end-user with additional water (C) to the desired concentration for use.

In an embodiment, a composition suitable for IRS application or a coating formulation containing a methoxyacrylate compound of Table 1 contains the active ingredient and a carrier, such as water, and may also one or more co-formulants selected from a dispersant, a wetter, an antifreeze, a thickener, a preservative, an emulsifier and a binder or sticker.

The methoxyacrylate compound of Table 1 is generally milled to a desired particle size, such as the particle size distribution d(0.5) is generally from 3 to 20, preferably 5 to 15, especially 7 to 12, μm.

Furthermore, it may be possible to ship the formulation to the end-user as a kit comprising at least
   a first component comprising at least one compound listed in Table 1 (A); and
   a second component comprising at least one polymeric binder (B).
   Further additives (D) may be a third separate component of the kit, or may be already mixed with components (A) and/or (B).

The end-user may prepare the formulation for use by just adding water (C) to the components of the kit and mixing.

The components of the kit may also be formulations in water. Of course it is possible to combine an aqueous formulation of one of the components with a dry formulation of the other component(s).

As an example, the kit can comprise
   one formulation of a compound listed in Table 1 (A) and optionally water (C); and
   a second, separate formulation of at least one polymeric binder (B), water as component (C) and optionally components (D).

Accordingly, in a further aspect the present invention provides a kit for treating a fibre, yarn, net and weave by coating wash resistant insecticidal properties thereto comprising: a first sachet comprising a pre-measured amount of at least one compound listed in Table 1, and a second sachet comprising a pre-measured amount of at least one polymeric binder. The resulting treated fibre, yarn, net and weave has imparted thereto the insecticidal properties needed for vector control, such as to control vector-carrying mosquitoes.

The concentrations of the components (A), (B), (C) and optionally (D) will be selected by the skilled artisan depending of the technique to be used for coating/treating.

In general, the amount of pesticide (A) may be up to 50, preferably 5 to 50, such as 10 to 40, especially 15 to 30, percent by weight, based on weight of the composition.

The amount of polymeric binder (B) may be in the range of 0.01 to 30, preferably 0.5 to 15, more preferably 1 to 10, especially 1 to 5, percent by weight, based on weight of the composition.

If present, in general the amount of additional components (D) is from 0.1 to 20, preferably 0.5 to 15, percent by weight, based on weight of the composition. If present, suitable amounts of pigments and/or dyestuffs are in general 0.01 to 5, preferably 0.1 to 3, more preferably 0.2 to 2, percent by weight, based on weight of the composition.

A typical formulation ready for use comprises 0.1 to 40, preferably 1 to 30, percent of components (A), (B), and optionally (D), the residual amount being water (C).

A typical concentration of a concentrate to be diluted by the end-user may comprise 5 to 70, preferably 10 to 60, percent of components (A), (B), and optionally (D), the residual amount being water (C).

The formulation of the present invention may be applied to polymeric material before their formation into the required products, e.g. while still a yarn or in sheet form, or after formation of the relevant products.

For the case of nets and/or weaves, a process for coating nets and/or weaves at least comprising the following steps:
a) treating the nets and/or weaves with the aqueous formulation according to the invention by any of the procedural steps selected from the group of
  (a1) passing the material through the formulation; or
  (a2) contacting the material with a roller that is partly or fully dipped into the formulation and drawing the formulation to the side of the material in contact with the roller, or
  (a3) submerging the material into the formulation; or
  (a4) spraying the formulation onto the material; or
  (a5) brushing the formulation onto or into the material; or
  (a6) applying the formulation as a foam; or
  (a7) coating the formulation onto material.
b) optionally removing surplus formulation by squeezing the material between rollers or by means of a doctor blade; and
c) drying the material.

In case the raw materials containing residues of preceding production processes, e.g. sizes, spin finishes, other auxiliaries and/or impurities, it may be beneficial to perform a washing step before the coating.

Specifically, the following details are important for the steps a), b), and c).

Step a1)

The formulation is applied by passing the material through the aqueous formulation. Said step is known by a person skilled in the art as padding. In a preferred embodiment the material is completely submerged in the aqueous formulation either in a trough containing the liquor or the material is passed through the formulation which is held between two horizontally oriented rollers. In accordance with the invention, the material may either be passed through the formulation or the formulation may be passed through the material. The amount of uptake of the formulation will be influenced by the stability of concentrated baths, the need for level distribution, the density of material and the wish to save energy costs for drying and curing steps. Usual liquor-uptakes may be 40 to 150 percent on the weight of material. A person skilled in the art is familiar with determining the optimum value. Step a1) is preferred for coating open-width material which is later tailored into nets.

For small-scale production or re-coating of non-treated nets, use of a simple hand-held roller may be sufficient.

Step a2)

It is further possible to apply the aqueous formulation on the material by a roller that is partly dipped into the dispersion thus applying the dispersion to the side of the material in contact with the roller (kiss-rolling). By this method it is possible to coat only one side of the material which is advantageous if e.g. direct contact of the human skin with insecticide-treated material is to be avoided.

Coating of the material in step a1), a2) or a3) is typically carried out at temperatures from 10 to 70 degrees centigrade, preferably 15 to 50 degrees centigrade, more preferably 20 to 40 degrees centigrade Step a4)

The spray may be applied in continuous processes or in batch-wise processes in suitable textile machines equipped with a spraying device, e.g. in open-pocket garment washer/extractors. Such equipment is especially suitable for impregnating ready-made nets.

Step a6)

A foam comprises less water than the dispersion mentioned above. The drying process may therefore be very short. The treatment may be performed by injecting gas or blends of gas (e.g., air) into it. The addition of surfactants, preferably with film-forming properties, may be required. Suitable surfactants and the required technical equipment are known to persons skilled in the art.

Step a7)

A coating process may preferably carried out in a doctor-blade process. The process conditions are known to a person skilled in the art.

Step b)

The surplus emulsion is usually removed by squeezing the material, preferably by passing the material through rollers as known in the art thus achieving a defined liquor uptake. The squeezed-off liquor may be re-used. Alternatively, the surplus aqueous emulsion or aqueous dispersion may be removed by centrifuging or vacuum suction.

Step c)

Drying may be performed at ambient temperatures. In particular, such a passive drying may be carried out in hot-dry climate. Of course, the drying process may be accelerated applying elevated temperatures. An active drying process would normally be performed during high scale processing. The drying is in general carried out temperatures below 200 degrees centigrade Preferred temperatures are from 30 to 170 degrees centigrade, more preferably at room temperature. The temperature choice is determined by the thermal stability of the insecticide in the formulation and the thermal stability of the non-living material impregnated.

For the method according to the invention aqueous formulation comprising at least one pigment and/or at least one dyestuff may be used so that the material is not only coated with the methoxyacrylate pesticide but in addition also coloured at the same time.

In a further aspect, the present invention provides a method for treating a fibre, yarn, net and weave by coating wash resistant insecticidal properties thereto comprising (i) preparing a treatment composition, which comprises at least one compound listed in Table 1, (ii) treating said fibre, yarn, net and weave and (iii) drying the resulting treated a fibre, yarn, net and weave.

The polymeric binder (B) can be dispersed in an aqueous formulation and comprises one or more fluorinated acrylic copolymers useful in the water and oil resistant formulations includes copolymer prepared by the polymerization of a perfluoroalkyl acrylate monomer and a comonomer, especially an acrylate monomer. The binder may also be fluorocarbon resins (as described in WO 2006/128870.

Only water is used as solvent for the formulation. However, trace amounts of organic solvents miscible with water may be present. Examples of solvents comprise water-miscible alcohols, e.g. monoalcohols such as methanol, ethanol or propanol, higher alcohols such as ethylene glycol or polyether polyols and ether alcohols such as butyl glycol or methoxypropanol. Preferably the content of an organic solvent is no more than 5 percent by weight (based on component (C), more preferably no more than 1 percent by weight (based on component (C), in particular no more than 0.1 percent by weight, based on component (C).

Depending on the intended use of the non-living material to be treated the formulation according to the present invention may further comprise one or more components or additives (D) selected from preservatives, detergents, fillers, impact modifiers, anti-fogging agents, blowing agents, clarifiers, nucleating agents, coupling agents, fixative agents, cross-linking agents, conductivity-enhancing agents (antistats), stabilizers such as antioxidants, carbon and oxygen radical scavengers and peroxide decomposing agents and the like, flame retardants, mould release agents, agents having UV protecting properties, spreading agents, anti-blocking agents, anti-migrating agents, foam-forming agents, anti-soiling agents, thickeners, further biocides, wetting agents, plasticizers and film-forming agents, adhesive or anti-adhesive agents, optical brightening (fluorescent whitening) agents, pigments and dyestuffs.

A typical amount of the polymeric binder (B) is from 0.01 to 10 percent by weight (dry weight) of the (dry) weight of the material. As a general guideline, the weight ratio between insecticide and binder (B) should approximately be constant with a value depending on the insecticidal and migratory ability of the insecticide, i.e. the higher the amount the insecticide the higher also the amount of binder (B).

Preferred amounts of binder (B) are from 0.1 to 5 percent by weight, more preferably 0.2 to 3 percent by weight of the (dry) weight of the material.

The coated material can comprise at least one pigment and/or at least one dyestuff. The amount of the at least one pigment and/or dyestuff is in general from 0.05 to 10 percent by weight, preferably 0.1 to 5 percent by weight, more preferably 0.2 to 3.5 percent by weight of the (dry) weight of the material.

The method of coating or treating the non-living material is not limited to a specific technology. Coating may be performed by dipping or submerging the non-living substrate into the formulation or by spraying the formulation onto the surface of the non-living material. After treating the treated non-living substrate may be dried simply at ambient temperatures.

Accordingly, no sophisticated technology is necessary for the coating, and therefore the coating process may be carried out by the end-user itself in at low-scale.

For instance, a typical end-user may coat/treat a net itself, e.g. within its household, using the formulation according to the present invention. For this purpose, it is in particular advantageous to use a kit as herein defined.

In an embodiment, the present invention provides a polymer, a fibre, a thread, a yarn, a net or weave comprising one or more compounds of the invention (listed in Table 1), where also incorporated can be one or more other customary materials used to make such a polymer, and the polymer, a fibre, a thread, a yarn, a net or weave optionally can further incorporate one or more other insecticides and/or synergists.

In an embodiment, the present invention provides a net or weave incorporated with one or more methoxyacrylate compounds (listed in Table 1), which optionally further incorporates one or more other insecticides and/or synergists.

As described in the art, the methoxyacrylate compound of Table 1 useful in the methods and other aspects of the present invention can be used alone or in combination with another insecticide, synergist, insect repellent, chemosterilant, flame retardant, UV protector/absorber, and/or additives for controlling release characteristics.

When used in accordance with the invention, the methoxyacrylate compounds of Table 1 may be used alone to control a mosquito or used in combination with one or other known insecticides and/or one or more additives (such as synergists)—in polymers for making non-living substrates, such as nets and weaves, for formulations for treating non-living substrates, such as nets and weaves, in IRS products and space-spraying products.

In an embodiment, the present invention provides a composition (useful for coating a polymeric material or a product therefrom, or a useful as a spray product) comprising one or more compounds of the invention, which optionally further comprises one or more other insecticide and/or synergists and one or more other additives.

Examples of synergists are piperonylbutoxide (PBO), sebacic esters, fatty acids, fatty acid esters, vegetable oils, esters of vegetable oils, alcohol alkoxylates and antioxidants.

Suitable sebacic esters are for example dimethyl sebacate, diethyl sebacate, dibutyl sebacate, dibenzyl sebacate, bis(N-succinimidyl)sebacate, bis(2-ethylhexyl)sebacate, bis(1-octyloxy-2,2,6,6-tetramethyl-4-piperidyl)sebacate, bis(2,2,6,6-tetramethyl-4-piperidyl)sebacate and bis(1,2,2,6,6-pentamethyl-4-piperidinyl)sebacate (BLS292).

Suitable fatty acids are (preferably mono- or polyunsaturated) fatty acids having a chain length of 12 to 24 carbon atoms, for example palmitoleic acid, oleic acid, elaidic acid, vaccenic acid, icosenic acid, cetoleic acid, erucic acid, nervonic acid, linoleic acid, alpha-linolenic acid, gamma-linolenic acid, arachidonic acid, timnodonic acid, clupanodonic acid and cervonic acid. Particular preference is given to oleic acid, linoleic acid, alpha-linolenic acid and gamma-linolenic acid.

Suitable fatty acid esters are preferably methyl or ethyl esters of the above-recited fatty acids. Methyl esters are particularly preferred. Fatty acids and their esters can each also be present in mixtures.

Useful vegetable oils include all plant-derivable oils customarily usable in agrochemical compositions. As examples there may be mentioned sunflower oil, rapeseed oil, olive oil, castor oil, colza oil, maize kernel oil, cottonseed oil and soybean oil. Rapeseed oil is preferred.

Suitable esters of vegetable oils are methyl or ethyl esters of the above-recited oils. Methyl esters are preferred.

Antioxidants useful as additives include for example butylhydroxytoluene, butylhydroxyanisole and L-ascorbic acid.

Plant essential oils may also be used in an indoor residual spray compositions; examples are those selected from citronella, peppermint oil, d-limonene and *abies sibirica*. These plant essential oil materials are known and used for other uses and can be prepared by a skilled artisan by employing known methods and also are available commercially.

In addition to at least one defined active ingredient from the group of methoxyacrylate (a compound listed in Table 1), the methods, compositions, polymer, product, substrate and/or integrated mosquito management solution according to the invention may contain one or more further insecticidally active ingredients. Particularly examples are one or more active ingredients from the class of organophosphates, pyrethroids, carbamates or neonicotinoid, and also DDT, indoxacarb, nicotine, bensultap, cartap, spinosad, camphechlor, chlordane, endosulfan, gamma-HCH, HCH, heptachlor, lindane, methoxychlor, acetoprole, ethiprole, fipronil, pyrafluprole, pyriprole, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacyrl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, *Bacillus thuringiensis* strains, spirodiclofen, spiromesifen, spirotetramat, 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8), flonicamid, amitraz, propargite, flubendiamide, chloranthraniliprol, thiocyclam hydrogen oxalate, thiosultap-sodium, azadirachtin, *Bacillus* spec., *Beauveria* spec., Metarrhizium spec., *Paecilomyces* spec., Thuringiensin, *Verticillium* spec., aluminium phosphid, methylbromide, sulfurylfluorid, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonylbutoxid, kaliumoleat, pyridalyl, sulfluramid, tetradifon, tetrasul, triarathene and verbutin.

In a further aspect, the present invention provides a method for protecting a mammal, including a human, against mosquitoes, the method comprising applying to the mosquito or to a locus of potential or known interaction between the mammal and the mosquito, a vector control solution comprising a mosquitocidally effective amount of a compound selected from the group consisting of a methoxyacrylate compound as defined in Table 1.

Another aspect of the invention is a method for controlling the spread of a vector-borne disease, comprising: identifying an mosquito vector; and contacting the mosquito vector or its environment with a vector control solution comprising a mosquitocidally effective amount of a compound selected from the group consisting of a methoxyacrylate compound as defined in Table 1.

An aspect of the invention also includes a mosquitocidal method which comprises contacting a mosquito or its environment with a vector control solution comprising an mosquitocidally effective amount of a compound selected from the group consisting of a methoxyacrylate compound as defined in Table 1.

The present invention also provides a method, comprising: (i) identifying a locus of potential or known interaction between a mosquito vector and a mammal, including a human, susceptible to pathogenic disease infection when contacted by such vector and (ii) positioning a vector control solution at the locus, wherein the solution includes a mosquitocidally effective amount of a compound selected from the group consisting of a methoxyacrylate compound as defined in Table 1.

The present invention through control of mosquitos would also be expected to control the many viruses carried by such vectors. As an example, control of the mosquitos of the genus *Aedes* by use of one or more of the defined compounds Table 1, as part of a vector control solution, may control the Zika infections. Examples of mosquitos reported to spread the Zika virus are the *Aedes* mosquitoes, such as *Aedes aegypti* and *Aedes albopictus*. Accordingly, in an aspect, the present invention provide a method of controlling Zika virus infection, wherein one or more of the defined compounds Table 1 is present in a mosquitocidally effective amount in the vicinity of *Aedes* mosquitoes, such as *Aedes aegypti* and *Aedes albopictus*. In the vicinity of the mosquitoes is meant areas where mosquitos are likely to be present, such as in the environment in general, specifically in a room, or at the site of a mosquito biting an individual or mammal, for example, on the skin surface.

In each of the methods according to present invention, the vector control solution is preferably one or more of a composition, a product and a treated article, each comprising a compound selected from the group consisting of a methoxyacrylate compound as defined in Table 1.

A "fibre" as used in the present invention refers only to a fine, threadlike piece, generally made of natural material, such as cotton, or jute.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The disclosure in the present application makes available each and every combination of embodiments disclosed herein.

The following Examples serve to illustrate the invention. They do not limit the invention.

Temperatures are given in degrees Celsius; mixing ratios of solvents are given in parts by volume.

The Examples which follow serve to illustrate the invention. The compounds of the invention can be distinguished from other similar compounds by virtue of greater efficacy at low application rates, which can be verified by the person skilled in the art using the experimental procedures outlined in the Examples below, using lower concentrations if necessary, for example 10 ppm, 5 ppm, 2 ppm, 1 ppm or 0.2 ppm; or lower application rates, such as 300, 200 or 100, mg of Al per m2.

EXAMPLES

Preparation Examples

Example 1: Preparation of methyl (E)-2-[2-[(5-tert-butyl-1,3,4-oxadiazol-2-yl)oxy]phenyl]-3-methoxy-prop-2-enoate (compound 2)

Step 1:
2-tert-butyl-5-(p-tolylsulfonyl)-1,3,4-oxadiazole

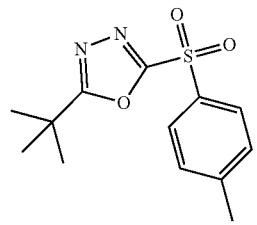 [SMILES: Cc1ccc(S(=O)(=O)c2nnc(C(C)(C)C)o2)cc1]

To a solution of KMnO$_4$ (1.67 grams, 1.3 equiv., 10.47 mmol) in water (150 ml) was added dropwise a solution of 2-tert-butyl-5-(p-tolylsulfanyl)-1,3,4-oxadiazole (2 g, 8.06 mmol) in glacial acetic acid (30 ml). After 2 h an aqueous solution of sodium metabisulphite was added until the mixture was decolorized. The mixture was filtered and the solid was washed with water, then recrystallized from ethanol to give 2-tert-butyl-5-(p-tolylsulfonyl)-1,3,4-oxadiazole (1.00 g, 3.57 mmol, 44% yield).

Step 2: Methyl (E)-2-[2-[(5-tert-butyl-1,3,4-oxadiazol-2-yl)oxy]phenyl]-3-methoxy-prop-2-enoate

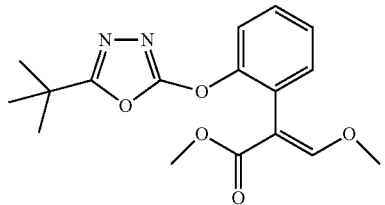 [SMILES: CO/C=C(/C(=O)OC)c1ccccc1Oc1nnc(C(C)(C)C)o1]

To a solution of methyl (E)-2-(2-hydroxyphenyl)-3-methoxy-prop-2-enoate (100 mg, 0.48 mmol; prepared as described in Example 3 of EP 0242081 A) in DMF (2 ml) at 0° C. was added 2-tert-butyl-5-(p-tolylsulfonyl)-1,3,4-oxadiazole (404 mg, 3 equiv., 1.44 mmol) and K$_2$CO$_3$ (2 equiv., 0.96 mmol). The mixture was allowed to warm to room temperature and stirred for 72 h. The mixture was partitioned between diethyl ether and water. The aqueous layer was extracted two times with ether. The combined organic layers were washed with water and brine, dried with MgSO$_4$, filtered and concentrated under reduced pressure. Column chromatography 100% cyclohexane to cyclohexane/ethyl acetate (70:30) gave methyl (E)-2-[2-[(5-tert-butyl-1,3,4-oxadiazol-2-yl)oxy]phenyl]-3-methoxy-prop-2-enoate (102 mg, 0.30 mmol, 64% yield).

Example 2: Methyl(E)-3-methoxy-2-[2-[[(E)-[(2E)-2-methoxyimino-1-methyl-butylidene]amino]-oxymethyl]phenyl]prop-2-enoate (compound 4)

Step 1: (2E)-2-Hydroxyiminopentan-3-one

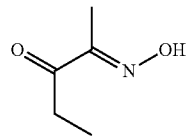

To a solution of pentan-3-one (6 g, 69.7 mmol) in toluene (30 ml) at 0° C. was added hydrogen chloride (2 mol/L) in diethyl ether (35 ml, 1 equiv., 69.7 mmol, 2 mol/L) dropwise. After the addition was complete a solution of isoamylnitrite (10.7 ml, 1.1 equiv., 76.63 mmol) in diethyl ether (20 ml) was added dropwise. The mixture was stirred at 0° C. for 2 h, then allowed to warm to room temperature and stirred for 16 h. Water (25 ml) was added and the mixture was extracted three times with 2M NaOH. The combined aqueous layers were made slightly acidic with 2M HCl and extracted three times with dichloromethane. The combined organic layers were dried with MgSO$_4$, filtered and concentrated under reduced pressure to give (2E)-2-hydroxyiminopentan-3-one (5.27 g, 45.8 mmol, 66% yield).

Step 2: (3E)-3-Methoxyiminopentan-2-one oxime

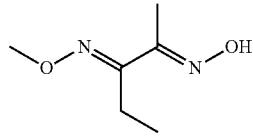

To a solution of (2E)-2-hydroxyiminopentan-3-one (2.8 g, 24 mmol) in toluene (30 ml) was added methoxyamine hydrochlorid (40% in H$_2$O) (1.2 equiv., 29 mmol). The mixture was heated to 65° C. and triethylamine (1.75 equiv., 43 mmol) was added dropwise. The mixture was heated at 65° C. for 3 h. The mixture was cooled to room temperature and acidified with conc. HCl. The organic layer was collected and extracted three times with 2 M NaOH. The combined extracts were made acidic with conc. HCl and extracted three times with ethyl acetate. The combined organic layers were dried with MgSO$_4$, filtered and concentrated. Column chromatography 100% dichloromethane to dichloromethane/methanol (90:10) gave (3E)-3-methoxyiminopentan-2-one oxime (2.2 g, 15 mmol, 63% yield).

Step 3: Methyl (E)-3-methoxy-2-[2-[[(E)-[(2E)-2-methoxyimino-1-methyl-butylidene]amino]oxymethyl]phenyl]prop-2-enoate

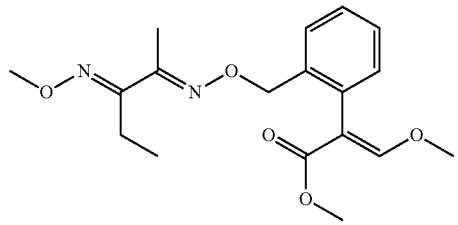

To a stirred solution of methyl (E)-2-[2-(bromomethyl)phenyl]-3-methoxy-prop-2-enoate (2.5 g, 8.8 mmol; prepared as in J. Agric. Food. Chem, 2007, 55, 5697-5700) in acetone (8 ml) was added (3E)-3-methoxyiminopentan-2-one oxime (1.5 g, 1.2 equiv., 11 mmol) and K$_2$CO$_3$ (1.8 g, 1.5 equiv., 13 mmol). The mixture was heated to 60° C. for 72 h. The mixture was cooled to room temperature, filtered and concentrated under reduced pressure. Column chromatography 100% cyclohexane to cyclohexane/ethyl acetate (80:20) gave methyl (E)-3-methoxy-2-[2-[[(E)-[(2E)-2-methoxyimino-1-methyl-butylidene]amino]oxymethyl]-phenyl]prop-2-enoate (1.8 g, 5.2 mmol, ~59% yield). Minor impurities were removed by a second chromatography: 100% dichloromethane to dichloromethane/ethyl acetate (95:5).

Example 3: Methyl (E)-2-[2-[(4-tert-butyl-1,3,5-triazin-2-yl)oxy]phenyl]-3-methoxy-prop-2-enoate (compound 5)

Step 1: N'-cyano-2,2-dimethyl-propanamidine

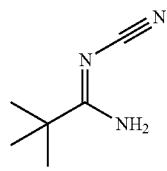

The HCl salt of 2,2-dimethylpropanamidine (2.5 g, 18.3 mmol) was dissolved in water (8 ml) and sodium hydrogencyanamide (1.17 g) was added. The mixture was stirred at room temperature for 4 h. The solid was filtered in dried in vacuum to give N'-cyano-2,2-dimethyl-propanamidine (1.17 g, 9.3 mmol, 51%).

Step 2: 2-tert-butyl-4-chloro-1,3,5-triazine

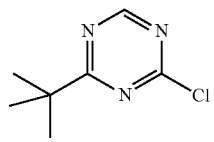

POCl₃ (1.54 g) was added into dry acetonitrile (10 ml). Dry DMF was added dropwise over 10 minutes. Then N'-cyano-2,2-dimethyl-propanamidine (1.17 g, 9.3 mmol) in dry acetonitrile (25 ml) was added over a period of 25 minutes and the resulting mixture was stirred for 4.5 h at room temperature. The mixture was poured into water (100 ml) and extracted with CH₂Cl₂ (4×40 ml). The combined organic phases were dried with MgSO₄, filtered and concentrated to provide 2-tert-butyl-4-chloro-1,3,5-triazine as an oil (1.15 g, 6.7 mmol, 72%).

Step 3: Methyl (E)-2-[2-[(4-tert-butyl-1,3,5-triazin-2-yl)oxy]phenyl]-3-methoxy-prop-2-enoate

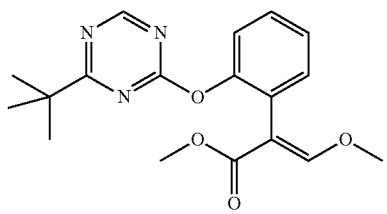 [SMILES: CO/C=C(/C(=O)OC)c1ccccc1Oc1ncnc(C(C)(C)C)n1]

To a stirred solution of methyl (E)-2-(2-hydroxyphenyl)-3-methoxy-prop-2-enoate (1.54 g, 7.4 mmol; prepared as described in Example 3 of EP 0242081 A) in DMF (25 ml) was added under cooling (−0° C.) potassium carbonate (930 mg) followed by addition of 2-tert-butyl-4-chloro-1,3,5-triazine (1.15 g, 6.7 mmol). The reaction mixture was stirred at −0° C. for 1.5 h. The reaction mixture was poured into water and extracted with diethyl ether. The organic layer was dried over Na₂SO₄, filtered and concentrated. The crude reaction mixture was then purified by column chromatography using ethyl acetate-hexane (1:3) to give methyl (E)-2-[2-[(4-tert-butyl-1,3,5-triazin-2-yl)oxy]phenyl]-3-methoxy-prop-2-enoate (330 mg, 0.96 mmol, 14%).

Example 4: Methyl (E)-3-methoxy-2-[2-[[5-(trifluoromethyl)-1,3,4-thiadiazol-2-yl]oxy]phenyl]-prop-2-enoate (compound 6)

Step 1: 2-Bromo-5-(trifluoromethyl)-1,3,4-thiadiazole

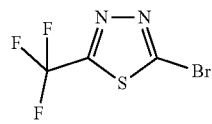

To a stirred solution of 5-(trifluoromethyl)-1,3,4-thiadiazol-2-amine (5.0 g, 29.5 mmol) in aqueous HBr was added a solution of sodium nitrite (4.48 g, 64.97 mmol) in 125 ml water dropwise at 0° C. during 2 h and stirred for another 2 h. The reaction was diluted with ethyl acetate and brine. The ethyl acetate layer was separated and the aqueous part was washed twice with ethyl acetate. The combined organic layers were washed with brine, dried over sodium sulfate and concentrated. The crude compound was then purified by flash chromatography using 15% ethyl acetate/hexane to give 2-bromo-5-(trifluoromethyl)-1,3,4-thiadiazole (1.2 g, 5.1 mmol, 17% yield).

Step 2: Methyl (E)-3-methoxy-2-[2-[[5-(trifluoromethyl)-1,3,4-thiadiazol-2-yl]oxy]phenyl]-prop-2-enoate

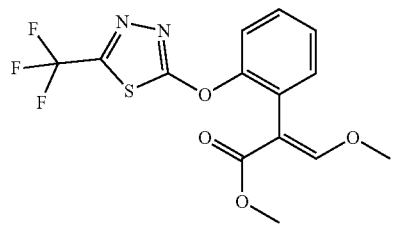 [SMILES: CO/C=C(/C(=O)OC)c1ccccc1Oc1nnc(C(F)(F)F)s1]

To a stirred solution of 2-bromo-5-(trifluoromethyl)-1,3,4-thiadiazole (710 mg, 3.41 mmol) in 10 ml DMF methyl (E)-2-(2-hydroxyphenyl)-3-methoxy-prop-2-enoate (1.19 g, 5.12 mmol; prepared as described in Example 3 of EP 0242081 A) was added followed by potassium carbonate. The reaction mixture turned brownish. TLC showed complete consumption of starting material after 3 days. The reaction was partitioned between ethyl acetate (50 ml) and water (50 ml). The organic layer was washed subsequently with water (20 ml) and brine (20 ml). The organic layer was dried over Na₂SO₄, filtered and concentrated. The crude reaction mixture was then purified by column chromatography using 20-30% ethyl acetate-hexane to give methyl (E)-3-methoxy-2-[2-[[5-(trifluoromethyl)-1,3,4-thiadiazol-2-yl]oxy]phenyl]-prop-2-enoate (1.1 g, 3.0 mmol, 88% yield).

Example 5: Methyl (E)-2-[2-[(3-tert-butyl-1,2,4-thiadiazol-5-yl)oxy]phenyl]-3-methoxy-prop-2-enoate (compound 7)

Step 1: 3-tert-Butyl-5-chloro-1,2,4-thiadiazole

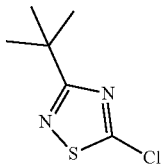

To a stirred solution of the HCl salt of 2,2-dimethylpropanamidine (1.6 g, 11.8 mmol) in dichloromethane (30 ml) at −15° C. was added trichloromethyl thiohypochlorite (2.0 g, 10.8 mmol) and aqueous sodium hydroxide solution (2.36 g, 59 mmol; dissolved in 12 ml water) slowly. After addition, the temperature of the reaction mixture was slowly raised to room temperature and stirring was continued for 3 h. The reaction mixture was diluted with dichloromethane and washed with water (50 ml×3). The combined organic layer was dried over $Na_2SO_4$, filtered and concentrated under reduced pressure to give 3-tert-butyl-5-chloro-1,2,4-thiadiazole (1.7 g, 9.6 mmol, 89% yield).

Step 2: 3-tert-Butyl-5-methylsulfonyl-1,2,4-thiadiazole

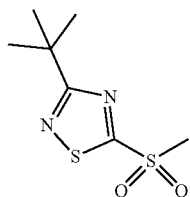

To a stirred solution of 3-tert-butyl-5-chloro-1,2,4-thiadiazole (260 mg, 1.47 mmol) in ethylene glycol mono ethyl ether (2 ml) was added at room temperature sodium methanesulfinate (150 mg, 1.47 mmol). After the addition the temperature of the reaction mixture was slowly raised to 100° C. and stirring was continued for 1 h. The reaction was monitored by TLC and after the completion of the reaction the mixture was allowed to cool down to room temperature. The reaction mixture was partitioned between water (5 ml) and $CH_2Cl_2$ (10 ml). The organic layer was dried over $Na_2SO_4$, filtered and concentrated under reduced pressure to give the crude material. The crude material was purified by column chromatography using 15-20% ethyl acetate/hexane as an eluent to afford 3-tert-butyl-5-methylsulfonyl-1,2,4-thiadiazole (325 mg, 1.48 mmol, quantitative yield).

Step 3: Methyl (E)-2-[2-[(3-tert-butyl-1,2,4-thiadiazol-5-yl)oxy]phenyl]-3-methoxy-prop-2-enoate To a stirred solution of methyl (E)-2-(2-hydroxyphenyl)-3-methoxy-prop-2-enoate (100 mg, 0.48 mmol; prepared as described in Example 3 of EP 0242081) in dry DMF (2 ml) were added 3-tert-butyl-5-methylsulfonyl-1,2,4-thiadiazole (127 mg, 0.57 mmol) and $K_2CO_3$ (100 mg, 0.72 mmol) at room temperature and stirring was continued for 17 h. The reaction was monitored by TLC and after completion of the reaction the mixture was partitioned between ethyl acetate (10 ml) and brine (10 ml). The organic layer was dried over $Na_2SO_4$, filtered and concentrated under reduced pressure. The crude material was purified by column chromatography using 15-20% ethyl acetate/hexane as an eluent to give methyl (E)-2-[2-[(3-tert-butyl-1,2,4-thiadiazol-5-yl)oxy]phenyl]-3-methoxy-prop-2-enoate (90 mg; 0.26 mmol 54% yield).

Example 6: Methyl (E)-2-[2-[[4-(trifluoromethyl)-2-pyridyl]oxy]phenyl]-3-methoxy-prop-2-enoate (compound 8)

Step 1: Methyl (E)-2-[2-[[6-chloro-4-(trifluoromethyl)-2-pyridyl]oxy]phenyl]-3-methoxy-prop-2-enoate To a solution of 2-chloro-6-fluoro-4-(trifluoromethyl)pyridine (184 mg, 1.1 equiv., 0.924 mmol) in DMF (5 ml) at room temperature was added methyl (E)-2-(2-hydroxyphenyl)-3-methoxy-prop-2-enoate (175 mg, 0.84 mmol; prepared as described in Example 3 of EP 0242081 A) and $K_2CO_3$ (174 mg, 1.5 equiv., 1.26 mmol). The mixture was stirred at room temperature for 16 h. The mixture was partitioned between diethyl ether and water. The aqueous layer was extracted twice with ether.

The combined organic layers were washed with water and brine, dried with $MgSO_4$, filtered and concentrated under reduced pressure. Column chromatography cyclohexane 100% to cyclohexane/ethyl acetate (80:20) gave methyl (E)-2-[2-[[6-chloro-4-(trifluoromethyl)-2-pyridyl]oxy]phenyl]-3-methoxy-prop-2-enoate (170 mg, 0.439 mmol, 52% yield).

Step 2: Methyl (E)-2-[2-[[4-(trifluoromethyl)-2-pyridyl]oxy]phenyl]-3-methoxy-prop-2-enoate

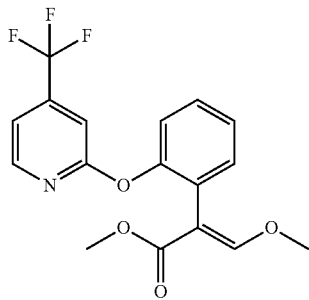 [SMILES: CO/C=C(/C(=O)OC)c1ccccc1Oc1cc(C(F)(F)F)ccn1]

To a solution of (E)-2-[2-[[6-chloro-4-(trifluoromethyl)-2-pyridyl]oxy]phenyl]-3-methoxy-prop-2-enoate (235 mg, 0.606 mmol) in methanol (5 ml) was added palladium on activated carbon (10%) (118 mg, 1.1041 mmol) and ammonium formate (77 mg, 2 equiv., 1.21 mmol). The mixture was heated at 60° C. for 3 h, then cooled to room temperature, filtered through celite and concentrated under reduced pressure. The residue was partitioned between water and ethyl acetate. The aqueous layer was extracted with ethyl acetate. The combined organic layers were dried and concentrated. Column chromatography 100% cyclohexane to 40% cyclohexane/ethyl acetate (60:40) gave methyl (E)-2-[2-[[4-(trifluoromethyl)-2-pyridyl]oxy]phenyl]-3-methoxy-prop-2-enoate (141 mg, 0.399 mmol, 66% yield).

Example 7: methyl (E)-3-methoxy-2-[2-[6-(trifluoromethyl)pyrimidin-4-yl]oxyphenyl]prop-2-enoate (compound 11)

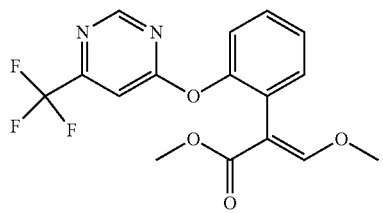 [SMILES: CO/C=C(/C(=O)OC)c1ccccc1Oc1cc(C(F)(F)F)ncn1]

To a solution of 4-chloro-6-(trifluoromethyl)pyrimidine (142 mg 0.78 mmol) in DMF (2 ml) at room temperature was added methyl (E)-2-(2-hydroxyphenyl)-3-methoxy-prop-2-enoate (162 mg, 0.78 mmol; prepared as described in Example 3 of EP 0242081 A) and $K_2CO_3$ (215 mg 1.5561 mmol). The mixture was stirred at room temperature for 48 h. The mixture was partitioned between diethyl ether and water. The aqueous layer was extracted with ether (x2). The combined organic layers were washed with water and brine, dried with $MgSO_4$, filtered and concentrated under reduced pressure. Column chromatography cyclohexane 100% to Cyclohexane-ethyl acetate (80:20) followed by a second column with dichloromethane to dichloromethane ethyl acetate (90:10) gave methyl (E)-3-methoxy-2-[2-[6-(trifluoromethyl)pyrimidin-4-yl]oxyphenyl]prop-2-enoate (74.6 mg, 0.211 mmol, 27% Yield).

Example 8: Methyl (E)-3-methoxy-2-[2-[5-(trifluoromethyl)thiazol-2-yl]oxyphenyl]prop-2-enoate (compound 13)

Step 1: 2-Bromo-5-(trifluoromethyl)thiazole

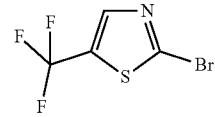

To a stirred and degassed solution of 5-(trifluoromethyl)thiazol-2-amine (590 mg, 3.8 mmol) in $CH_2Cl_2$ (5 ml), Cu(II)Br (867 mg, 3.88 mmol) and isoamyl nitrite (1.55 ml, 11.64 mmol) were added under argon atmosphere and stirred at room temperature for 1 h. The reaction was monitored by TLC. After completion of the reaction the mixture was quenched with ice water and extracted with pentane. The organic phase was washed with water and brine, dried over sodium sulphate, filtered and concentrated to give the crude compound. The crude compound was then purified by column chromatography using pentane as an eluent to give 2-bromo-5-(trifluoro-methyl)thiazole (-600 mg, 67% yield).

Step 2: 2-(2-Iodophenoxy)-5-(trifluoromethyl)thiazole

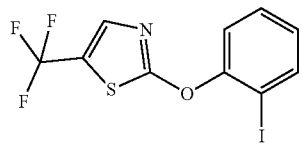 [SMILES: FC(F)(F)c1cnc(Oc2ccccc2I)s1]

To a stirred solution of 2-bromo-5-(trifluoro-methyl)thiazole (1.0 g, 4.2 mmol) and 2-iodophenol (1.0 g, 4.62 mmol) in NMP (10 ml) was added $Cs_2CO_3$ (2.05 g, 6.3 mmol) at room temperature and the reaction mixture was stirred for 4 h. The reaction was monitored by TLC. After completion of the reaction the mixture was quenched with ice water and extracted with ethyl acetate. The ethyl acetate layer was washed with water, brine, dried over sodium sulphate, filtered and concentrated to give a crude product. The crude product was purified by column chromatography to give 2-(2-iodophenoxy)-5-(trifluoromethyl)thiazole (770 mg, 2.07 mmol, 49% yield).

Step 3: Methyl (Z)-2-iodo-3-methoxy-prop-2-enoate

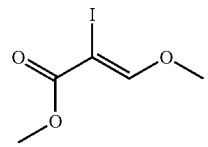

To a stirred solution of methyl (E)-3-methoxyprop-2-enoate (10.0 g, 86.2 mmol) in CH$_2$Cl$_2$ (170 ml), NIS (23.27 g, 103.4 mmol) and AcOH (10.34 g, 172.41 mmol) were added at 0° C. The reaction mixture was stirred at room temperature for 24 h. Then triethylamine (26.17 g, 258.6 mmol) was added and the resulting mixture was stirred for another 12 h at room temperature. The reaction mixture was then partitioned between CH$_2$Cl$_2$ (200 ml) and water (200 ml) and the aqueous layer was extracted with CH$_2$Cl$_2$. The combined organic layers were washed with saturated NaCl solution, dried over sodium sulphate, filtered and concentrated. The residue was purified by column chromatography on silica gel using 10% ethyl acetate—hexane as eluent to afford methyl (Z)-2-iodo-3-methoxy-prop-2-enoate (11.0 g, 45.5 mmol, 53% yield).

Step 4: Methyl (E)-3-methoxy-2-[2-[5-(trifluoromethyl)thiazol-2-yl]oxyphenyl]prop-2-enoate

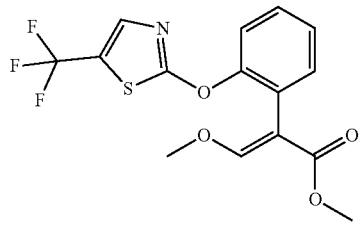 [SMILES: CO/C=C(/C(=O)OC)c1ccccc1Oc1ncc(C(F)(F)F)s1]

A) To a stirred suspension of Zn/Ag (1.35 g) in THE (7 ml), TMSCI (0.11 ml) was added at room temperature and the mixture was stirred at room temperature for 30 minutes. A degassed solution of TMEDA (0.96 g, 8.2 mmol) and methyl (Z)-2-iodo-3-methoxy-prop-2-enoate (2.0 g, 8.2 mmol) in THE (3 ml) was added and the resulting mixture was stirred at room temperature for 7 h. THE solution was directly used for the cross-coupling reaction.

B) To a stirred solution of 2-(2-iodophenoxy)-5-(trifluoromethyl)thiazole (400 mg, 1.07 mmol) in THE (3 ml) which was degassed with argon, Pd(PPh$_3$)$_4$ (62 mg, 0.054 mmol) and the Zink reagent in THE (7 ml) were added. The reaction mixture was stirred at 65° C. for 16 h. After completion of the reaction, the mixture was cooled to room temperature and quenched with saturated aqueous ammonium chloride solution, extracted with ethyl acetate, washed with brine, dried over sodium sulphate, filtered and concentrated to give the crude compound. The crude compound was purified by column chromatography using ethyl acetate-hexane (10-12%) to give methyl (E)-3-methoxy-2-[2-[5-(trifluoromethyl)thiazol-2-yl]oxyphenyl]prop-2-enoate (240 mg, 0.67 mmol 63% yield).

Example 9: Methyl (E)-3-methoxy-2-[2-[[3-(trifluoromethyl)-2-pyridyl]oxymethyl]phenyl]prop-2-enoate (compound 19)

Step 1: 2-[(2-Iodophenyl)methoxy]-3-(trifluoromethyl)pyridine

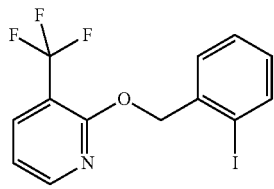 [SMILES: FC(F)(F)c1cccnc1OCc1ccccc1I]

To a solution of (2-iodophenyl)methanol (3.5 g, 15 mmol) in THE (1.7 ml) was added at room temperature sodium hydride (720 mg, 1.2 equiv., 18 mmol, 60%). The mixture was stirred at room temperature for 1 h. Then 2-chloro-3-(trifluoromethyl)pyridine (3.3 g, 1.2 equiv., 18 mmol) was added and the mixture was heated at reflux for 72 h. The mixture was cooled to room temperature and water was added. The mixture was extracted three times with ethyl acetate. The combined organic extracts were washed with brine and dried with MgSO$_4$, filtered and then concentrated under reduced pressure. Purification by column chromatography with gradient elution 100% cyclohexane to cyclohexane/ethyl acetate (80:20) gave 2-[(2-iodophenyl)-methoxy]-3-(trifluoromethyl)pyridine (4.41 g, 11.6 mmol, 78% yield)

Step 2: Methyl (E)-3-methoxy-2-[2-[[3-(trifluoromethyl)-2-pyridyl]oxymethyl]phenyl]prop-2-enoate

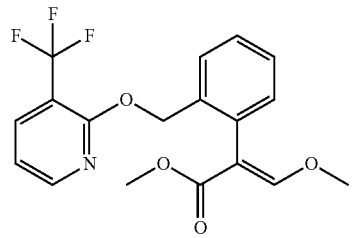 [SMILES: CO/C=C(/C(=O)OC)c1ccccc1COc1ncccc1C(F)(F)F]

A) To a suspension of activated zinc dust (1.35 g, 20.1 mmol) in THE (4 ml) was added chloro-trimethylsilane (100 μl, 0.772 mmol). The mixture was stirred for 20 min before the addition of a solution of methyl (Z)-2-iodo-3-methoxy-prop-2-enoate (2 g, 8.26 mmol) and N,N,N',N'-tetramethylethane-1,2-diamine (1.24 mL, 8.2 mmol) dropwise. The mixture was stirred for 3 h and then allowed to settle. The solution of iodo-[(Z)-2-methoxy-1-methoxycarbonyl-vinyl] zinc; N,N,N',N'-tetramethylethane-1,2-diamine was used in the next step.

B) Iodo-[(Z)-2-methoxy-1-methoxycarbonyl-vinyl]zinc; N,N,N',N'-tetramethylethane-1,2-diamine (8.2 mmol, 8.2 mmol) was added to a solution of 2-[(2-iodophenyl)methoxy]-3-(trifluoromethyl)pyridine (2.2 g, 5.8 mmol) and Pd(PPh$_3$)$_4$ (50 mg, 0.05 equiv., 0.29 mmol) in THF (5 ml). The mixture was heated to 65° C. for 4 h. The mixture was quenched by addition of saturated aqueous NH$_4$Cl solution. The mixture was extracted with ethyl acetate. The organic layer washed with brine, dried with MgSO$_4$, filtered and concentrated under reduced pressure. Column chromatography 100% cyclohexane to cyclohexane/ethyl acetate (60:40) gave methyl (E)-3-methoxy-2-[2-[[3-(trifluoromethyl)-2-pyridyl]oxymethyl]phenyl]prop-2-enoate (1.24 g, 3.38 mmol, 58% yield).

Example 10: Methyl (E)-3-methoxy-2-[2-[[3-(trifluoromethyl)pyrazin-2-yl]oxymethyl]phenyl]prop-2-enoate (compound 20)

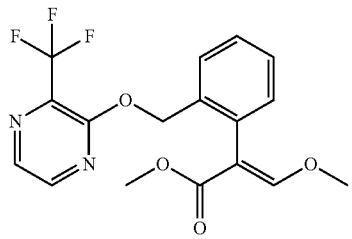 [SMILES: CO/C=C(/C(=O)OC)c1ccccc1COc1nccnc1C(F)(F)F]

To a suspension of 3-(trifluoromethyl)pyrazin-2-ol (100 mg, 0.609 mmol) in benzene (5 ml, 55.4 mmol) was added $Ag_2CO_3$ (203 mg, 1.2 equiv., 0.731 mmol) and methyl (E)-2-[2-(bromomethyl)-phenyl]-3-methoxy-prop-2-enoate (174 mg, 0.609 mmol; prepared as in J. Agric. Food. Chem, 2007, 55, 5697-5700). The mixture was heated at 80° C. for 72 h. The mixture was cooled to room temperature, diluted with dichloromethane, filtered and concentrated. The material was purified by column chromatography cyclohexane 100% to cyclohexane/ethyl acetate (60:40) followed by reversed phase chromatography (27 mg, 0.073 mmol, 12% yield).

Table 3 & 4 below lists the compounds of the invention 1 to 23 and comparative compounds respectively.

The table 3 & 4 contains literature references for known compounds and/or physical state or melting point and/or 1H-NMR data. The following abbreviations are used: s=singlet, d=doublet, t=triplet, q=quartet, m=multiplet, m.p.=melting point, ppm=parts per million.

BIOLOGY EXAMPLES

Example B1: *Aedes aegypti* (Yellow fever mosquito)

The individual wells of a twelve (12) well tissue culture plates were treated with 100 µl of an ethanol solution containing a test compound at 20 ppm concentration. Once the deposits were dry, five non-blood fed adult female *Aedes aegypti* (between two to five days old) were added to each well, and sustained with a 10% sucrose solution in a cotton wool plug. Assessment of the knockdown after 1 hour, and mortality after 48 hours was carried out.

In case of multiple tests, the mean value is reported. Results for the compounds of the invention and comparative compounds are shown in Table B1.

Example B2: *Anopheles stephensi* (Indian malaria mosquito)

The individual wells of a twelve (12) well tissue culture plates were treated with 100 µl of an ethanol solution containing a test compound at 20 ppm concentration. Once the deposits were dry, five non-blood fed adult female *Anopheles stephensi* (between two to five days old) were added to each well, and sustained with a 10% sucrose solution in a cotton wool plug. Assessment of the knockdown after 1 hour, and mortality after 48 hours was carried out.

In case of multiple tests, the mean value is reported. Results for the compounds of the invention and comparative compounds are shown in Table B2.

Example B3: *Aedes aegypti* or *Anopheles stephensi*

The individual wells of six (6) well tissue culture plates were treated with 250 µl of an ethanol solution containing a test compound at a defined concentration. Once the deposits were dry, ten non-blood fed adult female *Aedes aegypti* or *Anopheles stephensi* (each between two to five day old) were added to each well, and sustained with a 10% sucrose solution in a cotton wool plug.

Assessment of the mortality was carried out at 48 hours. Each treatment was replicated twice, with the mean mortality recorded.

Results for certain compounds of the invention and comparative compounds are shown in Table B3.

Example 84: Cross Resistance Studies

The Individual wells of six (6) well tissue culture plates were treated with 250 µl of an ethanol solution containing a test compound at a defined concentrations. Once the deposits were dry, ten non-blood fed adult female mosquitoes from strains with characterised insecticide resistance mechanisms were added to each well, and sustained with a 10% sucrose solution in a cotton wool plug. In each study, a set of plates were infested with a known insecticide susceptible strain of mosquitoes from the same genera as the resistant strains.

Assessment of the knockdown after 60 minutes and mortality after 24 hours was carried out. Each treatment was replicated a minimum of four times, with the mean knockdown or mortality recorded.

TABLE 3 methoxyacrylate compounds: compounds 1 to 23 (of the invention)

| Compound no. | Literature references/ CAS | | m.p. [° C.] | 1H-NMR [ppm] |
|---|---|---|---|---|
| 1 | WO 9518789 Table 1, compound No. 1.24 171276-46-3 | | 76-78 | In $CDCl_3$: 1.98 (s, 3H), 2.03 (s, 3H), 3.68 (s, 3H), 3.82 (s, 3H), 3.92 (s, 3H), 5.10 (s, 2H), 7.12-7.18 (m, 1H), 7.27-7.37 (m, 2H), 7.43-7.49 (m, 1H), 7.58 (s, 1H). |

TABLE 3-continued
methoxyacrylate compounds: compounds 1 to 23 (of the invention)
| Compound no. | Literature references/ CAS | | m.p. [° C.] | 1H-NMR [ppm] |
|---|---|---|---|---|
| 2 | WO 9505368 Table 1, compound No. 8 163619-68-9 | 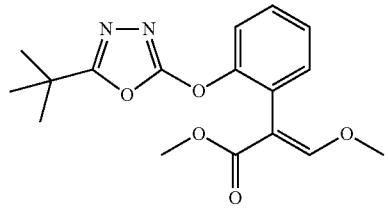 [SMILES: CO/C=C(/C(=O)OC)c1ccccc1Oc1nnc(C(C)(C)C)o1] | gum | In CDCl$_3$: 1.41 (s, 9H), 3.67 (s, 3H), 3.83 (s, 1H), 7.27-7.35 (m, 2H), 7.38-7.43 (m, 1H), 7.56-7.60 (m, 1H), 7.61 (s, 1H) |
| 3 | | 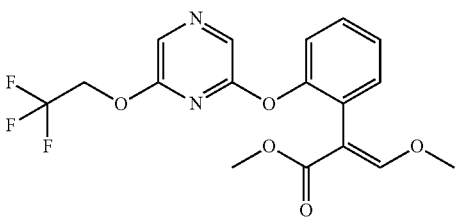 [SMILES: CO/C=C(/C(=O)OC)c1ccccc1Oc1cncc(OCC(F)(F)F)n1] | gum | In CDCl$_3$: 3.58 (s, 3H), 3.63 (s, 3H), 4.52 (q, 2H), 7.1-7.5 (m, 4H), 7.42 (s, 1H), 7.89 (s, 1H), 8,00 (s, 1H). |
| 4 | | 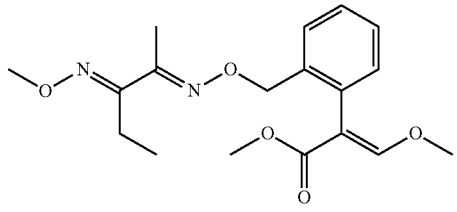 | 75-77 | In CDCl$_3$: 1.01 (t, 3H), 2.02 (s, 3H), 2.68 (q, 2H), 3.71 (s, 3H), 3.86 (s, 3H), 3.98 (s, 3H), 5.12 (s, 2H), 7.15-7.22 (m, 1H), 7.30-7.28 (m, 2H), 7.46-7.52 (m, 1H), 7.61 (s, 1H) |
| 5 | | 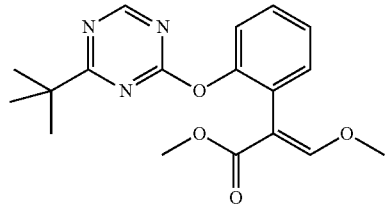 [SMILES: CO/C=C(/C(=O)OC)c1ccccc1Oc1ncnc(C(C)(C)C)n1] | 69-71 | In CDCl$_3$: 1.35 (s, 9H), 3.58 (s, 3H), 3.72 (s, 3H), 7.22-7.42 (m, 4H), 7.48 (s, 1H), 8.81 (s, 1H). |
| 6 | GB 2193495A Table 1, compound No. 115 115314-10-8 | 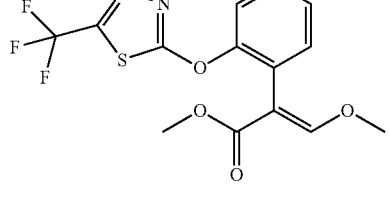 | 45-46 | 3.64 (s, 3H), 3.77 (s, 3H), 7.29-7.35 (m, 3H), 7.35-7.48 (m, 1H), 7.54 (s, 1H) |
| 7 | WO 9505368 Table 5, compound No. 8 163619-69-0 | 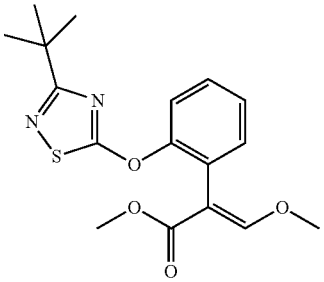 [SMILES: CO/C=C(/C(=O)OC)c1ccccc1Oc1nc(C(C)(C)C)ns1] | 64-66 | In CDCl$_3$: 1.36 (s, 9H), 3.58 (s, 3H), 3.70 (s, 3H), 7.29-7.40 (m, 4H), 7.54 (s, 1H). |

TABLE 3-continued methoxyacrylate compounds: compounds 1 to 23 (of the invention)

| Compound no. | Literature references/ CAS | | m.p. [° C.] | 1H-NMR [ppm] |
|---|---|---|---|---|
| 8 | EP 242081 Table 1, compound No. 11 114077-75-7 | | 78-80 | In CDCl3: 3.55 (s, 3H), 3.70 (s, 3H), 6.99 (d, 1H), 7.14 (d, 1H), 7.18 (d, 1H), 7.23-7.28 (m, 1H), 7.31-7.40 (m, 2H), 7.42 (s, 1H), 8.32 (d, 1H) |
| 9 | | | gum | In CDCl₃: 1.32 (s, 9H), 3.62 (s, 3H), 3.77 (s, 3H), 6.83 (s, 1H), 7.1-7.5 (m, 4H), 7.52 (s, 1H), 8.79 (s, 1H). |
| 10 | WO 9505368, example 5 Table 9, compound No. 8 163619-70-3 | | 103-105 | In CDCl₃: 1.30 (s, 9H), 3.63 (s, 3H), 3.76 (s, 3H), 7.27-7.45 (m, 4H), 7.54 (s, 1H). |
| 11 | | | 102-104 | In CDCl₃: 3.59 (s, 3H), 3.72 (s, 3H), 7.09 (s, 1H), 7.19 (d, 1H), 7.31-7.44 (m, 3H), 7.45 (s, 1H), 8.88 (s, 1H). |
| 12 | WO 9007493 Table, compound No. 116 130923-57-8 | | gum | In CDCl₃: 1.05 (s, 3H), 1.07 (s, 3H), 1.79 (s, 3H), 2.5 (m, 1H), 3.68 (s, 3H), 3.80 (s, 3H), 4.98 (s, 2H), 7.10-7.16 (m, 1H), 7.24-7.36 (m, 2H), 7.43-7.50 (m, 1H), 7.56 (s, 1H). |
| 13 | | | gum | In CDCl₃: 3.62 (s, 3H), 3.74 (s, 3H), 7.28-7.36 (m, 3H), 7.37-7.42 (m, 1H), 7.51-7.53 (m, 2H). |

TABLE 3-continued
methoxyacrylate compounds: compounds 1 to 23 (of the invention)
| no. | Literature references/ CAS | | m.p. [° C.] | 1H-NMR [ppm] |
|---|---|---|---|---|
| 14 | | 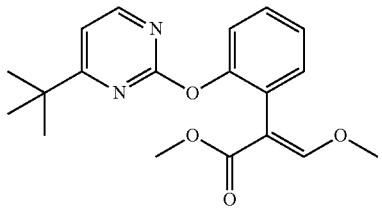 [SMILES: CO/C=C(/C(=O)OC)c1ccccc1Oc1nccc(C(C)(C)C)n1] | gum | In CDCl$_3$: 1.30 (s, 9H), 3.53 (s, 3H), 3.68 (s, 3H), 6.98 (d, 1H), 7.2-7.4 (m, 4H), 7.42 (s, 1H), 8.40 (d, 1H). |
| 15 | WO 9218487 Example 5 Table 1, compound No. 260 145945-47-7 | 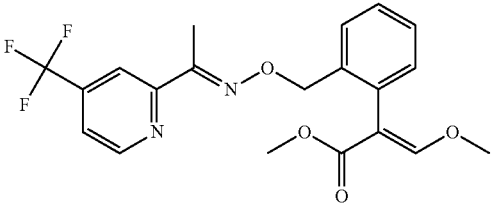 | 83-85 | In CDCl$_3$: 2.35 (s, 3H), 3.69 (s, 3H), 3.82 (s, 3H), 5.21 (s, 2H), 7.12-7.58 (m, 5 H), 7.62 (s, 1H), 8.13 (s, 1H), 8.74 (d, 1H). |
| 16 | | 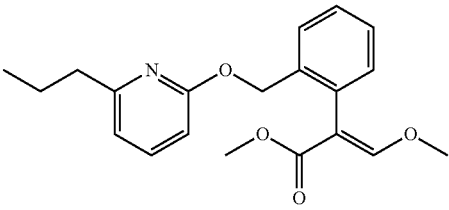 [SMILES: CCCc1cccc(OCc2ccccc2/C(=C\OC)C(=O)OC)n1] | gum | |
| 17 | | 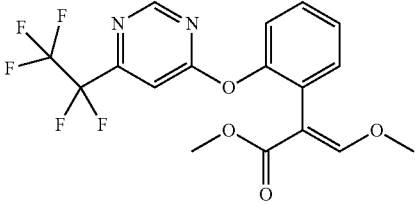 [SMILES: CO/C=C(/C(=O)OC)c1ccccc1Oc1cc(C(F)(F)C(F)(F)F)ncn1] | 65-66 | In CDCl$_3$: 3.6 (s, 3H), 3.7 (s, 3H), 7.15 (s, 1H), 7.2-7.5 (m, 4 H), 7.5 (s, 1H), 8.9 (s, 1H). |
| 18 | WO 9218487 Table 1, compound No. 270 145945-57-9 | 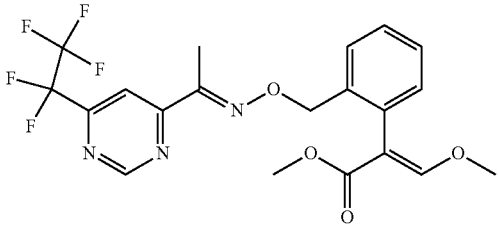 [SMILES: CO/C=C(/C(=O)OC)c1ccccc1CO/N=C(\C)c1cc(C(F)(F)C(F)(F)F)ncn1] | gum | In CDCl$_3$: 2.32 (s, 3H), 3.64 (s, 3H), 3.82 (s, 3H),5.26 (s, 2H),7.19-7.549 (m, 4H),7.63 (s, 1H), 8.23 (s, 1H), 8.33 (s, 1H). |
| 19 | | 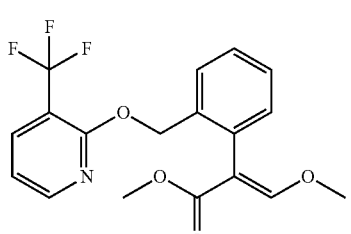 | gum | In CDCl$_3$: 3.71 (s, 3H), 3.84 (s, 3H), 5.42 (s, 2H), 6.92-7.01 (m, 1H), 7.15-7.20 (m, 1H), 7.31-7.41 (m, 2H), 7.62 (s, 1H), 7.60-7.68 (m, 1H), 7.86-7.90 (m, 1H), 8.28-8.33 (m, 1H). |

TABLE 3-continued methoxyacrylate compounds: compounds 1 to 23 (of the invention)

| Compound no. | Literature references/ CAS | Structure | m.p. [° C.] | 1H-NMR [ppm] |
|---|---|---|---|---|
| 20 | | | 81-83 | In CDCl$_3$: 3.71 (s, 3H), 3.86 (s, 3H), 5.43 (s, 2H), 7.18-7.23 (m, 1H), 7.33-7.41 (m, 2H), 7.58-7.62 (m, 1H), 7.63 (s, 1H), 8.22 (d, 1H), 8.31 (d, 1H). |
| 21 | | | amorphous | |
| 22 | Pesticide Science 1999, 55(2), 197-198. 222291-33-0 | | 69-71 | |
| 23 | | | gum | In CDCl$_3$: 3.70 (s, 3H), 3.85 (s, 3H), 5.30 (s, 2H), 7.10-7.20 (m, 1H), 7.30-7.40 (m, 3H), 7.50-7.60 (m, 1H), 7.66 (s, 1H). |

TABLE 4 methoxyacrylate compounds: comparative compounds A to AD

| Compound no. | Literature references/CAS | Structure | m.p. [° C.] | 1H-NMR [ppm] |
|---|---|---|---|---|
| A | CSAA383699 EP 382375 131860-33-8 Azoxystrobin | | | |

TABLE 4-continued methoxyacrylate compounds: comparative compounds A to AD

| Compound no. | Literature references/CAS | | m.p. [° C.] 1H-NMR [ppm] |
|---|---|---|---|
| B | WO 9521153
171276-50-9 | | 36-38 |
| C | WO 2000040537
229977-93-9
Fluacrypyrim | | |
| D | GB 2193495
115314-13-1 | | solid |
| E | EP 278595
117428-19-0 | | gum |
| F | EP 373775
131376-48-2 | | solid |
| G | WO 9218487
145945-43-3 | | 87-88 |

TABLE 4-continued methoxyacrylate compounds: comparative compounds A to AD

| Compound no. | Literature references/CAS | m.p. [° C.] | 1H-NMR [ppm] |
|---|---|---|---|
| H | WO 9218487 145945-41-1 | gum | |
| I | | 83-85 | |
| J | | gum | |
| K | WO 9505368 163619-62-3 | gum | |
| L | | gum | |
| M | WO 9505368 163619-74-7 | gum | |
| N | | gum | |

TABLE 4-continued
methoxyacrylate compounds: comparative compounds A to AD
| Compound no. | Literature references/CAS | | m.p. [° C.] | 1H-NMR [ppm] |
|---|---|---|---|---|
| O | | 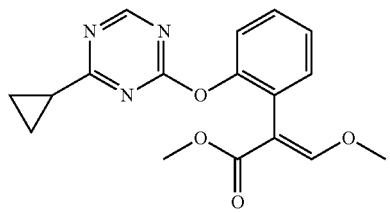 [SMILES: CO/C=C(/C(=O)OC)c1ccccc1Oc1ncnc(C2CC2)n1] | gum | |
| P | | 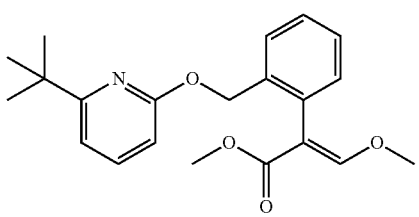 [SMILES: CO/C=C(/C(=O)OC)c1ccccc1COc1cccc(C(C)(C)C)n1] | gum | |
| Q | EP 414153<br>134725-65-8 | 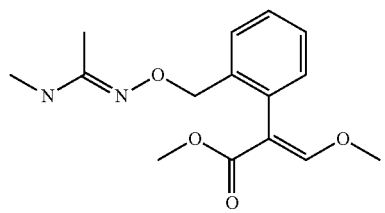 | 92-93 | |
| R | EP 936213<br>238410-11-2<br>Enoxastrobin | 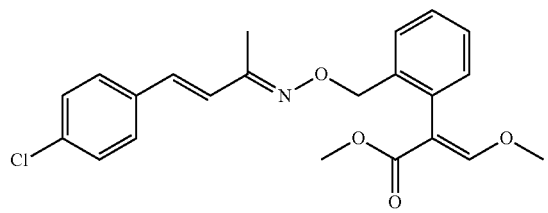 | | |
| S | WO 2005080344<br>862588-11-2<br>Pyraoxystrobin | 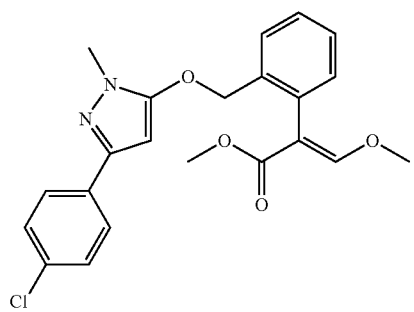 [SMILES: CO/C=C(/C(=O)OC)c1ccccc1COc1cc(-c2ccc(Cl)cc2)nn1C] | | |
| T | WO 2005044813<br>850881-70-8<br>Coumoxystrobin | 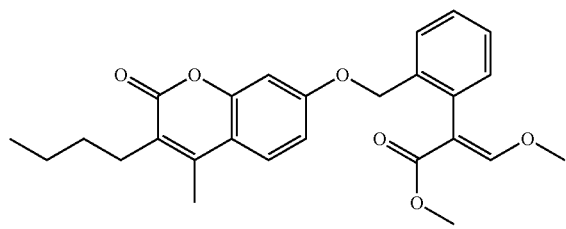 [SMILES: CCCCc1c(C)c2ccc(OCc3ccccc3/C(=C\OC)C(=O)OC)cc2oc1=O] | | |

TABLE 4-continued methoxyacrylate compounds: comparative compounds A to AD

| Compound no. | Literature references/CAS | | m.p. [° C.] | 1H-NMR [ppm] |
|---|---|---|---|---|
| U | WO 2010139271 1257598-43-8 Pyriminostrobin | | | |
| V | Journal of the American Chemical Society 2012, 134(27), 11168-11176. 1384120-13-1 | | 115-118 | |
| W | Journal of the American Chemical Society 2012, 134(27), 11168-11176. 1384120-10-8 | | 110-112 | |
| X | | | 122-124 | In CDCl3: 3.70 (s, 3H), 3.84 (s, 3H), 5.43 (broad s, 2H), 7.13-7.20 (m, 1H), 7.31-7.38 (m, 2H), 7.55-7.61 (m, 1H), 7.61 (s, 1H), 8.23 (d, 1H), 8.26 (d, 1H). |
| Y | | | 113-115 | In CDCl3: 1.29 (s, 9H), 3.65 (s, 3H), 3.76 (s, 3H), 7.32-7.43 (m, 3H), 7.47-7.52 (m, 1H), 7.41 (s, 1H). |

TABLE 4-continued methoxyacrylate compounds: comparative compounds A to AD

| Compound no. | Literature references/CAS | m.p. [° C.] | 1H-NMR [ppm] |
|---|---|---|---|
| Z | | 97-99 | In DMSO: 0.82 (t, 3H), 1.15 (d, 3H), 1.43-1.62 (, 2H), 2-62-2.72 (m, 1H), 3.53 (s, 3H), 3.76 (s, 3H), 7.28-7.38 (m, 2H), 7.35 (t, 1H), 7.52 (d, 1H), 7.66 (s, 1H). |
| AA | | gum | In CDCl$_3$: 1.30 (s, 9H), 3.61 (s, 3H), 3.76 (s, 3H), 6.84 (s, 1H), 7.21-7.37 (m, 4H), 7.52 (s, 1H). |
| AB | | gum | |
| AC | EP 278595 117428-22-5 Picoxystrobin | | |
| AD | | 92-94 | In CDCl$_3$: 1.26 (t, 3H), 2.71 (q, 2H), 3.66 (s, 3H), 3.77 (s, 3H), 7.33-7.48 (m, 4H), 7.44 (s, 1H). |

A comparison of the knockdown and mortality of the resistant strain of mosquitoes was made to that of the susceptible to identify evidence of cross resistance. Results are shown in Table B4.

Example B5: Bottle based cross resistance study

Based on the "CDC bottle assay" (described at http://www.cdc.gov/malaria/resources/pdf/fsp/ir_manual/ir_cdc_bioassay_en.pdf) 1 ml of ethanol containing a test compound at a defined concentration was added to a 250 ml glass bottle and the bottles were placed on a rolling table to coat the inner surfaces as the solvent evaporated. Once dry, twenty five non-blood fed adult female mosquitoes of the appropriate species and strains (each three day old) were aspirated from the stock culture and gently blown into the exposure bottles. The lid of the bottle was replaced and the bottle placed upright out of direct sun light under standard culture conditions, nominally 28C and 60-80% relative humidity.

A stopwatch was started, and the assessment of the knock-down were made after 15 minutes and 60 minutes. A mosquito was said to be knocked down if it was unable to stand, following the CDC definition. The bottles were replaced in an upright position when not being assessed.

After one hour the mosquitoes were carefully removed from the bottle with an aspirator and placed in a recovery cup. The mosquitoes were supplied with a 10% sucrose solution on a cotton wool bung, and stored under culture conditions. Assessments of the mortality were made after 24 hours.

Each treatment was replicated a minimum of four times, with the mean knockdown or mortality recorded. In each study, a set of bottles was infested with a known insecticide susceptible strain of mosquitoes from the same genera as the resistant strains. Results are shown in Tables B5.

Example B6: Evaluation of Residual Insecticidal Formulations

Experimental surfaces were sprayed with diluted residual insecticide formulation comprising a compound of the invention using an automated hydraulic sprayer fitted with an 8003 flat fan nozzle-corresponding to a coverage of 500 mg of compound per m2. Also applied was a lambda-cyhalothrin formulation (DEMAND 10 CS) such that there was 25 mg of lambda-cyhalothrin Al per m2. The pirimiphos-methyl formulation (ACETELLIC 300CS) was applied so that there was 1000 mg of pirimiphos-methyl Al per m2 (Table B6b).

The treated surfaces were stored in a controlled environment room at 28° C., ambient humidity and under low light conditions for 1 (one) week.

Three to five day old non-blood fed adult mosquitoes were taken from the culture and lightly anaesthetised with carbon dioxide. Ten females were selected and placed in a 250 ml plastic cup, retained with a net lid, provided with a 10% sucrose solution soaked in a cotton wool bung and held under culturing environmental conditions.

After twenty four hours, treated tiles, treated 7 days previously with a formulation, were removed from storage. A cup of the pre-selected mosquitoes were again lightly anaesthetised with carbon dioxide and transferred from the holding cup to the base of a 9 cm plastic Petri dish. The treated side of the relevant surface was placed over the Petri dish and held in place with an elastic band. Once the mosquitoes had recovered from the anaesthetic, ca. 1 minute, the treated surface attached to the Petri dish was placed on a holding rack, such that treated side was at an angle of 600 to the horizontal.

After one hour an assessment of mosquito knockdown was made. A mosquito was said to be knocked down if it was unable to right itself once it had fallen over. The mosquitoes were lightly anaesthetised again, and removed from the Petri dish exposure chamber and returned to the holding cups. The mosquitoes were supplied with a 10% sucrose solution soaked in a cotton wool bung and held under culturing environmental conditions. An assessment of mortality was made 24 hours after exposure. A mosquito was said to be dead if it is unable to right itself once it has fallen over. Results are shown in Tables B6.

Example B7: Evaluation of Insecticide Impregnated Polymer Surfaces

Preparation of polymeric sheets: Certain methoxyacrylate were Impregnated into three polymers: LDPE (low density polyethylene), HDPE (high density polyethylene) and PP (polypropylene) in different concentrations by mixing the respective polymer with a compound at high temperatures and the resultant polymeric material were then mould into thin discs or plaques.

Twenty four hours prior to the relevant assessment intervals, three to five day old non-blood fed adult mosquitoes were taken from the culture and lightly anaesthetised with carbon dioxide. Ten females were selected and placed in a 250 ml plastic cup, retained with a net lid, provided with a 10% sucrose solution soaked in a cotton wool bung and held under culturing environmental conditions.

After twenty four hours, impregnated polymer sheets (measuring about 150 mm in diameter and about 0.1 mm in thickness) were removed from storage and wrapped around the glazed side of an 11 cm ceramic tile and held in place with an elastic band. The age of the polymer sheets used are indicated in the tables below. A cup of the pre-selected mosquitoes were again lightly anaesthetised with carbon dioxide and transferred from the holding cup to the base of a 9 cm plastic Petri dish. The relevant impregnated polymer sheet was placed over the Petri dish and held in place with an elastic band. Once the mosquitoes had recovered from the anaesthetic, ca. 1 minute, the impregnated polymer sheet was placed on a holding rack, such that treated side was at an angle of 600 to the horizontal.

After one hour an assessment of mosquito knockdown was made. A mosquito was said to be knocked down if it was unable to right itself once it had fallen over. The mosquitoes were lightly anaesthetised again, and removed from the Petri dish exposure chamber and returned to the holding cups. The mosquitoes were supplied with a 10% sucrose solution soaked in a cotton wool bung and held under culturing environmental conditions. An assessment of mortality was made 24 hours after exposure. A mosquito was said to be dead if it is unable to right itself once it had fallen over. Results are shown in Tables B7.

TABLE B1

| Compound no. | Knockdown (%) | Mortality (%) |
| --- | --- | --- |
| 1 | 50 | 90 |
| 2 | 0 | 80 |
| 3 | 0 | 100 |
| 4 | 100 | 100 |
| 5 | 100 | 100 |
| 6 | 100 | 100 |
| 7 | 100 | 100 |
| 8 | 67 | 100 |
| 9 | 0 | 80 |
| 10 | 80 | 93 |
| 11 | 100 | 100 |
| 12 | 100 | 100 |
| 13 | 100 | 100 |
| 14 | 0 | 40 |
| 15 | 50 | 100 |
| 16 | 0 | 80 |
| 17 | 100 | 100 |
| 18 | 0 | 40 |
| 19 | 20 | 100 |
| 20 | 100 | 100 |
| 21 | 50 | 90 |
| 22 | 100 | 100 |
| 23 | 100 | 100 |
| A | 0 | 0 |
| B | 0 | 0 |
| C | 0 | 0 |
| D | 0 | 0 |
| E | 0 | 0 |
| F | 0 | 60 |
| G | 0 | 0 |
| H | 0 | 0 |
| I | 0 | 40 |
| J | 0 | 0 |
| K | 0 | 0 |
| L | 0 | 0 |
| M | 0 | 0 |
| N | 0 | 0 |
| O | 0 | 0 |
| P | 0 | 0 |
| Q | 0 | 0 |

TABLE B1-continued

| Compound no. | Knockdown (%) | Mortality (%) |
|---|---|---|
| R | 0 | 0 |
| S | 0 | 0 |
| T | 0 | 0 |
| U | 0 | 0 |
| V | 0 | 0 |
| W | 0 | 0 |
| X | 0 | 0 |
| Y | 0 | 0 |
| Z | 0 | 0 |
| AA | 0 | 0 |
| AB | 60 | 100 |
| AC | 0 | 40 |
| AD | 0 | 0 |
| Blank | 0 | 0 |
| DDT (10 ppm) | 35 | 90 |
| Lambda-cyhalothrin (2 ppm) | 92 | 100 |

TABLE B2

| Compound no. | Knockdown (%) | Mortality (%) |
|---|---|---|
| 1 | 40 | 100 |
| 2 | 40 | 100 |
| 3 | 100 | 100 |
| 4 | 80 | 100 |
| 5 | 100 | 100 |
| 6 | 100 | 100 |
| 7 | 67 | 100 |
| 8 | 100 | 100 |
| 9 | 100 | 100 |
| 10 | 93 | 100 |
| 11 | 80 | 100 |
| 12 | 100 | 100 |
| 13 | 100 | 100 |
| 14 | 0 | 100 |
| 15 | 40 | 100 |
| 16 | 20 | 100 |
| 17 | 100 | 100 |
| 18 | 100 | 100 |
| 19 | 40 | 100 |
| 20 | 100 | 100 |
| 21 | 100 | 100 |
| 22 | 100 | 100 |
| 23 | 20 | 100 |
| A | NT | NT |
| B | NT | NT |
| C | NT | NT |
| D | NT | NT |
| E | NT | NT |
| F | 60 | 100 |
| G | NT | NT |
| H | NT | NT |
| I | NT | NT |
| J | NT | NT |
| K | NT | NT |
| L | NT | NT |
| M | NT | NT |
| N | NT | NT |
| O | NT | NT |
| P | NT | NT |
| Q | NT | NT |
| R | NT | NT |
| S | NT | NT |
| T | NT | NT |
| U | NT | NT |
| V | NT | NT |
| W | NT | NT |
| X | NT | NT |
| Y | NT | NT |
| Z | NT | NT |
| AA | NT | NT |
| AB | 100 | 100 |
| AC | 100 | 100 |
| AD | NT | NT |
| Blank | 0 | 0 |
| DDT (10 ppm) | 70 | 80 |
| Lambda-cyhalothrin (2 ppm) | 83 | 100 |

Notes;
NT is not tested

TABLE B3

| | Aedes aegypti | Anopheles stephensi |
|---|---|---|
| ppm | 5 | 5 |
| compound | mortality (%) | mortality (%) |
| 1 | 74 | 100 |
| 2 | 90 | 100 |
| 4 | 78 | 98 |
| 5 | 85 | 100 |
| 6 | 66 | 98 |
| 7 | 78 | 95 |
| 8 | 100 | 100 |
| 10 | 47 | 93 |
| 12 | 43 | 100 |
| 13 | 78 | 100 |
| 15 | 70 | 95 |
| 16 | 20 | 95 |
| 17 | 5 | 55 |
| 18 | 70 | 100 |
| 19 | 75 | 100 |
| 20 | 70 | 100 |
| 21 | 85 | 100 |
| 22 | 100 | 100 |
| 23 | 60 | 93 |
| F | 30 | 20 |
| AB | 75 | 80 |
| AC | 4 | 75 |
| ppm | 5 | 5 |
| DDT | 85 | 59 |
| ppm | 0.2 | 0.2 |
| Lambda-cyhalothrin | 99 | 84 |

TABLE B4

| | Knockdown (%) | | | | | Mortality (%) | | | | |
|---|---|---|---|---|---|---|---|---|---|---|
| Compound | 4 | 6 | 7 | 10 | Permethrin | 4 | 6 | 7 | 10 | Permethrin |
| concentration/ppm | 2.00 | 2.0 | 2.50 | 1.56 | 2.50 | 2.00 | 2.00 | 2.50 | 1.56 | 2.50 |
| An. Gambiae Kisumu sus | 67 | 86 | 100 | 90 | 100 | 95 | 100 | 100 | 100 | 100 |
| An. Gambiae Kisumu rdl | 30 | 78 | 90 | 70 | 100 | 100 | 89 | 100 | 70 | 100 |
| An. Gambiae Tiassalé | 70 | 84 | 90 | 80 | 5 | 100 | 94 | 85 | 75 | 14 |

TABLE B4-continued

| | Knockdown (%) | | | | | Mortality (%) | | | | |
|---|---|---|---|---|---|---|---|---|---|---|
| Compound | 4 | 6 | 7 | 10 | Permethrin | 4 | 6 | 7 | 10 | Permethrin |
| *An. Arabiensis* Moz sus | 0 | 90 | 95 | 90 | 75 | 95 | 100 | 100 | 90 | 100 |
| *An. Arabiensis* Ndjamina | 100 | 100 | NT | 68 | NT | 100 | 100 | NT | 79 | NT |
| *Ae. aegypti* Caymon | 45 | 5 | 52 | 55 | 0 | 90 | 63 | 28 | 55 | 45 |
| *Ae. Aegypti* New Orleans | 75 | 95 | 38 | 70 | 91 | 100 | 100 | 100 | 85 | 100 |
| *An. stephensi* | 95 | 100 | 40 | 0 | 85 | 100 | 100 | 100 | 100 | 100 |

Notes;
NT is not tested

TABLE B5a

| | Knockdown (%) at 15 mins | | | | | Knockdown (%) at 60 mins | | | | | Mortality (%) | | | | |
|---|---|---|---|---|---|---|---|---|---|---|---|---|---|---|---|
| Compound | 4 | 6 | 7 | 10 | Permethrin | 4 | 6 | 7 | 10 | Permethrin | 4 | 6 | 7 | 10 | Permethrin |
| concentration/ppm | 20 | 20 | 20 | 20 | 20 | 20 | 20 | 20 | 20 | 20 | 20 | 20 | 20 | 20 | 20 |
| *An. Gambiae* Kisumu sus | 48 | 100 | 100 | 71 | 100 | 100 | 100 | 100 | 100 | 100 | 100 | 100 | 99 | 48 | 100 |
| *An. Gambiae* Tiassalé | 17 | 93 | 70 | 9 | 50 | 96 | 98 | 97 | 24 | 99 | 77 | 91 | 95 | 5 | 85 |
| *An. stephensi* | 10 | 83 | 37 | 57 | 97 | 100 | 100 | 100 | 100 | 100 | 80 | 100 | 100 | 30 | 100 |

TABLE B5b

| | Mortality (%) | | | |
|---|---|---|---|---|
| Compound | 8 | 13 | 22 | Permethrin |
| concentration/ppm | 25 | 25 | 25 | 25 |
| FUMOZ | 56 | 70 | 68 | 24 |
| VK7 | 20 | 61 | 96 | 3 |
| Kisumu sus | 61 | 94 | 100 | 99 |

TABLE B5c

| | Mortality (%) | |
|---|---|---|
| Compound | 7 | Permethrin |
| concentration/ppm | 25 | 25 |
| FUMOZ | 20 | 46 |
| VK7 | 19 | 4 |
| Kisumu sus | 97 | 100 |

Notes on mosquito species used in tables B4 & B5:

| Name | Species | Country of Origin | Phenotype |
|---|---|---|---|
| Kisumu | *Anopheles gambiae* | Kenya | Susceptible |
| Kisumu Rdl | *Anopheles gambiae* | Kenya | Dieldrin resistant |
| Tiassalé | *Anopheles gambiae* | Cote d'Ivoire | Pyrethroid resistant |
| Moz | *Anopheles arabiensis* | Mozambique | Susceptible |
| New Orleans | *Aedes aegypti* | USA | Susceptible |
| Cayman | *Aedes aegypti* | Grand Cayman | Pyrethroid, carbamate & DDT resistant |
| Ndjamina | *Anopheles arabiensis* | Chad | Pyrethroid resistant |
| VK7 | *Anopheles coluzzii* | Burkina Faso | Pyrethroid resistant |
| FUMOZ | *Anopheles funestus* | Mozambique | Pyrethroid resistant |
| SYN | *Anopheles stephensi* | India | Susceptible |

TABLE B6a

| formulation | compound | Knockdown (%) | Mortality (%) |
|---|---|---|---|
| 4A | 4 | 70 | 100 |
| 7A | 7 | 77 | 100 |
| 10A | 10 | 3 | 30 |
| Demand 10CS | Lambda-cyhalothrin | 100 | 100 |
| Water | control | 0 | 0 |

Notes:
Formulations 4A, 7A and 10A are each aqueous suspension concentrates containing about 10 wt % of active ingredient and also containinging conventional co-formulants in standard amounts, such as a dispersant, antifreeze, preservative, thickener, wetter, emulsier, and water as the carrier.

TABLE B6b

| formulation | compound | Knockdown (%) | Mortality (%) |
|---|---|---|---|
| 7B | 7 | 67 | 100 |
| ACTELLIC 300CS | pirimiphos-methyl | 0 | 100 |
| Water | control | 0 | 3 |

Notes:
Formulations 7B is an aqueous suspension concentrates containing about 10 wt % of active ingredient and also containinging conventional co-formulants in standard amounts, such as a dispersant, antifreeze, preservative, thickener, wetter, emulsier, and water as the carrier.

TABLE B7a age of impregnated polymer 4 to 6 weeks old against *Aedes aegypti* (knockdown)

| | AI content, | knock-down (%) | | |
|---|---|---|---|---|
| compound | wt % | LDPE | HDPE | PP |
| 4 | 2 | 63 | 53 | 63 |
| 6 | 2 | 100 | 87 | 83 |
| 7 | 2 | 100 | 83 | 67 |
| 10 | 2 | 23 | 80 | 0 |

TABLE B7a-continued age of impregnated polymer 4 to 6 weeks
old against *Aedes aegypti* (knockdown)

| compound | Al content, wt % | knock-down (%) LDPE | HDPE | PP |
|---|---|---|---|---|
| 17 | 2 | 100 | NT | NT |
| Permethrin | 2 | 100 | 100 | 87 |
| Blank | n/a | 0 | 0 | 0 |

TABLE B7b age of impregnated polymer 4 to 6 weeks
old against *Aedes aegypti* (mortality)

| compound | Al content, wt % | mortality (%) LDPE | HDPE | PP |
|---|---|---|---|---|
| 6 | 2 | 90 | 17 | 13 |
| 7 | 2 | 97 | 47 | 23 |
| 10 | 2 | 97 | 17 | 13 |
| Permethrin | 2 | 100 | 97 | 80 |
| Blank | n/a | 0 | 0 | 0 |

TABLE B7c age of impregnated polymer 4 to 6 weeks old
against *Anopheles stephensi* (knockdown)

| compound | Al content, wt % | knock-down (%) LDPE | HDPE | PP |
|---|---|---|---|---|
| 4 | 2 | 87 | 93 | 100 |
| 6 | 2 | 97 | 87 | 100 |
| 7 | 2 | 100 | 93 | 93 |
| 10 | 2 | 87 | 90 | 0 |
| Permethrin | 2 | 100 | 100 | 100 |
| Blank | n/a | 0 | 0 | 0 |

TABLE B7d age of impregnated polymer 4 to 6 weeks old
against *Anopheles stephensi* (mortality)

| compound | Al content, wt % | mortality (%) LDPE | HDPE | PP |
|---|---|---|---|---|
| 4 | 2 | 70 | 60 | 87 |
| 6 | 2 | 83 | 60 | 57 |
| 7 | 2 | 97 | 87 | 87 |
| 10 | 2 | 93 | 73 | 10 |
| Permethrin | 2 | 100 | 70 | 23 |
| Blank | n/a | 0 | 0 | 0 |

TABLE B7e age of impregnated polymer 6 to 8 weeks old
against *Anopheles stephensi* (knockdown)

| compound | Al content, wt % | knock-down (%) LDPE | HDPE | PP |
|---|---|---|---|---|
| 4 | 2 | 70 | 77 | 90 |
| 6 | 2 | 100 | 100 | 90 |
| 7 | 2 | 87 | 100 | 100 |
| 10 | 2 | 90 | 20 | 17 |

TABLE B7e-continued age of impregnated polymer 6 to 8 weeks old
against *Anopheles stephensi* (knockdown)

| compound | Al content, wt % | knock-down (%) LDPE | HDPE | PP |
|---|---|---|---|---|
| Permethrin | 2 | 100 | 100 | 100 |
| Blank | n/a | 0 | 0 | 0 |

TABLE B7f age of impregnated polymer 6 to 8 weeks old
against *Anopheles stephensi* (mortality)

| compound | Al content, wt % | mortality (%) LDPE | HDPE | PP |
|---|---|---|---|---|
| 4 | 2 | 100 | 80 | 100 |
| 6 | 2 | 77 | 63 | 80 |
| 7 | 2 | 100 | 87 | 77 |
| 10 | 2 | 100 | 17 | 93 |
| Permethrin | 2 | 100 | 97 | 67 |
| Blank | n/a | 10 | 7 | 13 |

TABLE B7g age of impregnated polymer 2 to 4 weeks
old against *Aedes aegypti* (knockdown)

| compound | Al content, wt % | knock-down (%) LDPE | HDPE | PP |
|---|---|---|---|---|
| 5 | 2 | 13 | 33 | 80 |
| 8 | 2 | 100 | 100 | n/t |
| 12 | 2 | 100 | 97 | 100 |
| 13 | 2 | 100 | 100 | 100 |
| 22 | 2 | 100 | 93 | 100 |
| Blank | n/a | 0 | 0 | 0 |

TABLE B7h age of impregnated polymer 2 to 4 weeks
old against *Aedes aegypti* (mortality)

| compound | Al content, wt % | mortality (%) LDPE | HDPE | PP |
|---|---|---|---|---|
| 5 | 2 | 13 | 27 | 40 |
| 8 | 2 | 100 | 53 | n/t |
| 12 | 2 | 100 | 27 | 80 |
| 13 | 2 | 93 | 73 | 87 |
| 22 | 2 | 100 | 93 | 100 |
| Blank | n/a | 0 | 7 | 13 |

TABLE B7i age of impregnated polymer 6 to 8 weeks
old against *Aedes aegypti* (knockdown)

| compound | Al content, wt % | knock-down (%) LDPE | HDPE | PP |
|---|---|---|---|---|
| 5 | 2 | 85 | 60 | 70 |
| 8 | 2 | 100 | 100 | n/t |
| 12 | 2 | 95 | 100 | 100 |
| 13 | 2 | 100 | 100 | 100 |

TABLE B7i-continued age of impregnated polymer 6 to 8 weeks
old against *Aedes aegypti* (knockdown)

| compound | Al content, wt % | knock-down (%) LDPE | HDPE | PP |
|---|---|---|---|---|
| 22 | 2 | 100 | 95 | 100 |
| Blank | n/a | 0 | 0 | 0 |

TABLE B7j age of impregnated polymer 6 to 8 weeks
old against *Aedes aegypti* (mortality)

| compound | Al content, wt % | mortality (%) LDPE | HDPE | PP |
|---|---|---|---|---|
| 5 | 2 | 95 | 15 | 55 |
| 8 | 2 | 100 | 75 | n/t |
| 12 | 2 | 55 | 75 | 70 |
| 13 | 2 | 95 | 65 | 35 |
| 22 | 2 | 100 | 100 | 100 |
| Blank | n/a | 0 | 10 | 5 |

TABLE B7k age of impregnated polymer 2 to 4 weeks old
against *Anopheles stephensii* (knockdown)

| compound | Al content, wt % | knock-down (%) LDPE | HDPE | PP |
|---|---|---|---|---|
| 5 | 2 | 80 | 100 | 90 |
| 8 | 2 | 100 | 100 | n/t |
| 12 | 2 | 100 | 100 | 100 |
| 13 | 2 | 100 | 100 | 100 |
| 22 | 2 | 100 | 100 | 100 |
| Blank | n/a | 7 | 0 | 0 |

TABLE B7l age of impregnated polymer 2 to 4 weeks old
against *Anopheles stephensii* (mortality)

| compound | Al content, wt % | mortality (%) LDPE | HDPE | PP |
|---|---|---|---|---|
| 5 | 2 | 87 | 80 | 67 |
| 8 | 2 | 100 | 100 | n/t |
| 12 | 2 | 100 | 97 | 97 |
| 13 | 2 | 100 | 100 | 100 |
| 22 | 2 | 93 | 97 | 93 |
| Blank | n/a | 3 | 10 | 0 |

TABLE B7m age of impregnated polymer 8 to 12 weeks old
against *Anopheles stephensii* (knockdown)

| compound | Al content, wt % | knock-down (%) LDPE | HDPE | PP |
|---|---|---|---|---|
| 5 | 2 | 70 | 50 | 20 |
| 8 | 2 | 90 | 100 | n/t |
| 12 | 2 | 30 | 100 | 100 |
| 13 | 2 | 100 | 90 | 100 |
| 22 | 2 | 80 | 90 | 100 |
| Blank | n/a | 0 | 0 | 0 |

TABLE B7n age of impregnated polymer 8 to 12 weeks old
against *Anopheles stephensii* (mortality)

| compound | Al content, wt % | mortality (%) LDPE | HDPE | PP |
|---|---|---|---|---|
| 5 | 2 | 100 | 20 | 50 |
| 8 | 2 | 100 | 80 | n/t |
| 12 | 2 | 0 | 30 | 70 |
| 13 | 2 | 80 | 0 | 10 |
| 22 | 2 | 100 | 90 | 100 |
| Blank | n/a | 0 | 0 | 0 |

The invention claimed is:

1. A method of controlling mosquitos, the method comprising: applying to a mosquito or to a locus of interaction of a mosquito a compound of Formula (VIII),

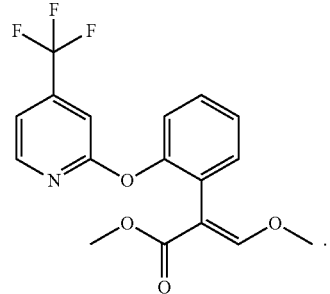 [SMILES: CO/C=C(/C(=O)OC)c1ccccc1Oc1cc(C(F)(F)F)ccn1 ; "."]

2. The method of claim 1, wherein the development of vector-borne diseases is reduced.

3. The method of claim 1, wherein the mosquito is a vector of pathogenic disease.

4. The method of claim 1, wherein applying comprises:
   (a) applying an effective amount of a liquid composition comprising the compound of Formula (VIII), and a polymeric binder, to a surface of a dwelling; or
   (b) placing a substrate or non-living material incorporated with the compound of Formula (VIII) within a dwelling.

5. The method of claim 1, wherein the mosquito is selected from *Aedes aegypti, Anopheles stephensi, Anopheles gambiae, Anopheles arabiensis, Anopheles coluzzii, Anopheles funestus*.

6. The method of claim 5, wherein the mosquito is selected from *Anopheles stephensi*.

7. The method of claim 1, wherein the applying is to the mosquito.

* * * * *

UNITED STATES PATENT AND TRADEMARK OFFICE
CERTIFICATE OF CORRECTION

| | | Page 1 of 1 |
|---|---|---|
| PATENT NO. | : 11,882,828 B2 | |
| APPLICATION NO. | : 15/579030 | |
| DATED | : January 30, 2024 | |
| INVENTOR(S) | : Hueter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1306 days.

Signed and Sealed this
First Day of July, 2025

Coke Morgan Stewart
*Acting Director of the United States Patent and Trademark Office*